United States Patent
Ali

(10) Patent No.: US 10,406,205 B1
(45) Date of Patent: Sep. 10, 2019

(54) METHOD FOR CURING DIABETES AND DAMAGED ORGANS AND TISSUES AFFECTED BY DIABETES

(71) Applicant: Jassim M. Hassan M. Ali, Safat (KW)

(72) Inventor: Jassim M. Hassan M. Ali, Safat (KW)

(*) Notice: Subject to any disclaimer, the term of this patent is extended or adjusted under 35 U.S.C. 154(b) by 0 days.

(21) Appl. No.: 16/292,725

(22) Filed: Mar. 5, 2019

(51) Int. Cl.
*A61K 38/17* (2006.01)
*A61P 3/10* (2006.01)
*A61K 9/00* (2006.01)

(52) U.S. Cl.
CPC ........ *A61K 38/1706* (2013.01); *A61K 9/0019* (2013.01); *A61P 3/10* (2018.01)

(58) Field of Classification Search
None
See application file for complete search history.

(56) References Cited

U.S. PATENT DOCUMENTS

| | | | |
|---|---|---|---|
| 5,658,594 A | | 8/1997 | Al-Hassan |
| 5,912,018 A | * | 6/1999 | Al-Hassan ............ A61K 35/60 424/520 |
| 8,551,532 B2 | * | 10/2013 | Al-Hassan ............ A61K 35/60 424/520 |

OTHER PUBLICATIONS

Al-Hassan et al. Comparative Biochemistry and Physiology Part B: Comparative Biochemistry vol. 88, Issue 3, 1987, pp. 813-822 (Year: 1987).*

Al-Hassan ("Diabetic ulcer healing preparations from the skin of the Arabian Gulf catfish (*Arius bilineatus* Val.): a novel and effective treatment," Int J Tissue React., 12, 121-35 (1990) (Year: 1990).*

Thomson et al. "Purification of a Toxic Factor From Arabian Gulf Catfish Epidermal Secretions," Toxicon, 36, 859-866, (1998) (Year: 1998).*

Al-Hassan et al. "Vasoconstrictor Components in the Arabian Gulf Catfish (*Arius thalassinus*, Ruppell) Proteinaceous Skin Secretion,"Toxicon, 24, pp. 1009-1014 (1986) (Year: 1986)*

Al-Hassan et al. "Catfish epidermal secretions in response to threat or injury," Marine Biology, 88, 117-123 (1985) (Year: 1985).*

Al-Hassan et al., "Skin Preparations from Catfish (*Arius bilineatus*, Val.) Contain a Lipid Which Inhibits Cancer Cell Survival In Vitro," The FASEB Journal, vol. 30, No. 1 supplement, Apr. 1, 2016.

Yang et al., "Abstract 2246: Anti-proliferalive activities of lipid fraction of extract from the skin of the catfish *Arius bilineatus*, Valenciennes," AACR Annual Meeting 2017; Apr. 1-5, 2017; Washington, DC.

Yang et al., "Anti-proliferative and anti-invasiveness of the lipid fraction of the skin extract from the catfish *Arius bilineatus*, valenciennes in human pancreatic, cancer is associated with regulation of lipid metabolism," Cancer Research 77, (13 Supplement):2246-2246, Jul. 2017.

* cited by examiner

*Primary Examiner* — Christina Bradley
(74) *Attorney, Agent, or Firm* — Richard C. Litman

(57) ABSTRACT

A method of treating diabetes can include administering a therapeutically effective amount of a composition comprising a soluble protein fraction obtained from epidermal gel secretions of catfish to a patient in need thereof. The soluble protein fraction can include soluble proteins and lipids from the epidermal gel secretions of catfish. The soluble protein fraction can include about 87% of the soluble proteins and about 13% of the lipids. The composition can be administered by intraperitoneal (IP) or sub-cutaneous (SC) injection.

16 Claims, 14 Drawing Sheets

METHOD FOR CURING DIABETES AND DAMAGED ORGANS AND TISSUES AFFECTED BY DIABETES

BACKGROUND

1. Field

The disclosure of the present patent application relates to use of a preparation from the epidermal gel secretions of catfish for therapeutic purposes, and particularly, to a method for treating diabetes mellitus using a preparation from the epidermal gel secretions of catfish.

2. Description of the Related Art

Diabetes is a disease caused by malfunction of the β cells of the Langerhans Islets, leading to the lack of production of insulin and the rise of glucose in the blood. Glucose being toxic, if not metabolized, will cause damage to vital organs and tissue. If not controlled, diabetes can lead to damage of several organs in the animal or human body, such as the pancreas, the kidney's, the liver, the heart, the testis, the eyes, as well as vital tissues such as the nervous tissues. Insulin administration is by far the best available treatment for controlling glucose levels in diabetic patients. As glucose levels in the blood fluctuate between insulin injections, the elevation of blood glucose between insulin injections from low to high levels could lead to damage of the organs, although at a slower rate. Insulin injection as a treatment does not lead to the cure of the damaged organs or lead to their regeneration. It merely slows down the rate of damage.

The Arabian Gulf catfish (*Arius bilineatus* (Valenciennes)) naturally exudes a proteinaceous gel-like material ("epidermal gel secretion") from its epidermis upon stress or injury. The epidermal gel secretion includes a complex mixture of biochemically and pharmacologically active components.

The epidermal gel secretion can provide numerous therapeutic benefits. Often times, however, the Arabian Gulf catfish produces venoms from its venomous spines and venom glands near its pectoral spines which mix with secretions on the catfish skin. Additionally, since the gelatinous secretion is exuded while the catfish is still alive, contaminants other than the venom (such as feces, vomit and blood) are also often mixed with the epidermal secretion. Thus, a method for treating diabetes solving the aforementioned problems is desired.

SUMMARY

A method of treating diabetes can include administering a therapeutically effective amount of a composition comprising a soluble protein fraction obtained by fractionating epidermal gel secretions of catfish to a patient in need thereof. The soluble protein fraction can include soluble proteins and lipids obtained by fractionating the epidermal gel secretions of catfish. The soluble protein fraction can include about 87% soluble proteins and about 13% lipids. The composition can be administered by intraperitoneal (IP) or sub-cutaneous (SC) injection. A method of preparing the soluble protein fraction can include collecting the epidermal gel secretion of catfish and fractionating the epidermal gel secretion to obtain the soluble protein fraction.

Fractionating the epidermal gel secretion of catfish can include mixing the catfish epidermal gel secretions with phosphate buffered saline to provide an extract, homogenizing the extract to provide a homogenized extract, and centrifuging the homogenized extract to provide a soluble protein fraction and an insoluble protein fraction. The soluble fraction can be freeze dried to provide a powdered soluble fraction. If desired, the insoluble protein fraction can be fractionated (in the manner described above for fractionating the EGS) to separate any undissolved soluble proteins therefrom. The additional soluble protein fraction extracted from the insoluble protein fraction can be added to the original soluble protein fraction to enrich the original soluble protein fraction.

The freeze-dried soluble fraction can be analyzed to determine a ratio of the concentration of soluble protein to lipids. Generally, it can be expected that the freeze-dried powdered soluble fraction includes about 87% soluble proteins. If the freeze-dried powdered soluble fraction includes less than about 13% lipids, however, the soluble fraction can be supplemented with lipids from an additional lipid fraction to provide a soluble protein fraction having about 87% soluble proteins and about 13% lipids. The additional lipid fraction can be obtained from the freeze-dried EGS. The therapeutic composition can include the soluble protein fraction having about 87% soluble proteins and about 13% lipids.

For administration of the composition, the soluble protein fraction can be taken out of deep freeze (−80° C.), dissolved in saline in phosphate buffer (pH 7.5), and maintained at temperatures ranging from about 4° C. to about 6° C. to be ready for administration. In an embodiment, the composition includes the soluble protein fraction dissolved in phosphate buffer saline. It is preferable to dissolve the soluble protein fraction and administer the composition when the composition is still cold, e.g., temperatures ranging from about 4° C. to about 6° C. For example, the composition can be maintained in crushed ice or in a refrigerator until it is ready to be administered.

These and other features of the present disclosure will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
FIG. 1A shows a histological slide of the pancreas of control, non-diabetic rats showing Langerhans Islets including the insulin secreting Beta cells.

A method of treating diabetes can include administering a therapeutically effective amount of a composition comprising a soluble protein fraction obtained from epidermal gel secretions of catfish to a patient in need thereof. The soluble protein fraction can include soluble proteins and lipids. The soluble protein fraction can include about 87% soluble proteins and about 13% lipids. The composition can be administered by intraperitoneal (IP) or sub-cutaneous (SC) injection. A method of preparing the soluble protein fraction can include collecting the epidermal gel secretion of catfish and fractionating the epidermal gel secretion to obtain the soluble protein fraction.

A method of preparing a therapeutic composition from the epidermal gelatinous secretion of catfish can include collecting epidermal gel secretions (EGS) from the catfish and fractionating the epidermal gel secretions to obtain a soluble protein fraction comprising about 87% soluble proteins and about 13% lipids. The therapeutic composition can include the soluble protein fraction comprising about 87% soluble proteins and about 13% lipids.

The soluble protein fractions described herein can be obtained from the epidermal gel secretions (EGS) of Arabian Gulf catfish, such as (*Arius bilineatus* (Valenciennes)). The Arabian Gulf catfish naturally exudes a gelatinous secretion through its skin after the catfish is shocked, e.g., threatened or injured. For example, once a catfish is caught, it will struggle as it is towed to the surface with the fishing hook still in its mouth (as the catfish is a bottom dweller). As the fish reaches the surface, it struggles to defend itself and to escape the reduction in water pressure. This will cause the fish to secrete the EGS along with one or more contaminants, such as venom from its venom glands, faeces from its anal pore, vomit from its mouth and through its gills, and blood through its gills if the fishing hook catches the gill rays. Shocking the fish can also be accomplished by thermal shock, physical abrasions, or neural stimulation. The fish can be washed one or more times to remove contaminants. While the fish is still alive, the fish can be held through its gills to induce production of additional EGS. The EGS without any remaining contaminants on the skin can be collected by a gentle mechanical scraping or suction of the skin. Preferably, the EGS is immediately frozen, e.g., in dry ice, then cooled to −80° C. (deep freeze) or kept frozen in liquid nitrogen, to limit microbial growth and prevent biochemical decomposition.

The soluble protein fractions described herein can include a mixture of highly active biochemical and pharmacological components. These include, for example, a plasma clotting factor that has been found to be specific to blood clotting factor X1, a hemolytic factor, platelet activating factors (PAFs) at unusually high levels (more than 5,000 times the threshold level required for normal platelet activation), and a hemagglutination factor. The soluble fraction can also include vaso-active components, phosphatases, including an acid phosphatase, a general esterase and a tyrosine specific esterase, and proteins with collagenase-like activities that cleave collagen into fragments. The soluble fraction can include a factor that activates phospholipase A2, tyrosine and serine/threonine protein phosphorylase, proteolytic and antimicrobial activities, leukotrienes, interleukin 1 and growth factors that affect macrophages and pancreatic β-cells, along with four protein components that are capable of binding human fibronectin. The lipids in the soluble fraction can include neutral lipids, phospholipids, and glycolipids. For example, the neutral lipids can include eicosanoids, cholesterol, triglycerides, fatty acids and steroids.

It should be understood that a therapeutic composition can be prepared from epidermal gel secretions of other species of catfish or any other aquatic or terrestrial creature (e.g., moray eels, slugs, and worms) that produces epidermal gel secretions having biologically active components similar to those present in the soluble protein fractions described herein.

As used herein, the term "about," when used to modify a numerical value, means within ten percent of that numerical value.

According to an embodiment, the method of preparing a therapeutic composition from the epidermal gelatinous secretion of catfish can include collecting epidermal gel secretions (EGS) from the skin of Arabian Gulf catfish (*Arius bilineatus* (Valenciennes)) and fractionating the EGS to provide a soluble protein fraction (SPF).

In an embodiment, the soluble protein fraction (SPF) can be extracted from the EGS by thawing the frozen EGS to a temperature ranging from about 4° C. to about 6° C. and mixing the thawed EGS with a suitable, non-toxic extraction buffer (e.g., saline in phosphate buffer at pH 7.5) to provide an extract. This step and all subsequent purification procedures can be carried out at about 4° C. to about 6° C. in the dark, unless otherwise indicated. The extraction buffer should not denature or affect the proteins in the EGS in any way. Preferably, the extraction buffer includes phosphate buffered saline having 0.05M ($NaH_2PO_4/Na_2HPO_4$) and 0.14M NaCl, pH 7.5. The thawed EGS can be mixed with an equal volume of the extraction buffer and homogenized, e.g., with an Ultra Truex (IKA) homogenizer. The homogenized extract can then be centrifuged to provide a soluble protein fraction (SPF) and an insoluble protein fraction. Centrifugation can separate insoluble filamentous proteins and cellular debris from a soluble fraction. Centrifugation can also remove contaminants such as microorganisms. The therapeutic composition is preferably free from insoluble components, as such components are not appropriate for intraperitoneal or sub-cutaneous injection and will not be absorbed and distributed if injected into an animal or human in this manner. Insoluble components can also clog the injection needle during injection. In an embodiment, the homogenate is centrifuged at 15,000 rpm for about ten to about fifteen minutes to provide the soluble fraction and the insoluble fraction. The soluble fraction can be freeze-dried and maintained at about −80° C. under nitrogen.

In an embodiment, the soluble protein fraction is freeze-dried and maintained at about −80° C. under nitrogen. The freeze-dried soluble fraction can be analyzed to determine a ratio of the concentration of soluble protein to lipids. In an embodiment, the powdered soluble fraction includes about 87% soluble proteins and about 13% lipids. If the powdered soluble fraction includes less than about 13% lipids, the powdered soluble fraction can be supplemented with lipids from an additional lipid fraction to achieve a soluble protein fraction having about 87% soluble proteins and about 13% lipids. The additional lipid fraction can be obtained from the freeze-dried EGS, as described herein. The therapeutic composition can include the soluble protein fraction having about 87% soluble proteins and about 13% lipids. The soluble fraction (SPF) (also referred to herein as "Fraction B") can be freeze-dried and stored at about −80° C. under nitrogen.

According to an embodiment, an additional soluble protein fraction can be separated from the insoluble fraction obtained from centrifugation. According to an embodiment, an insoluble fraction obtained from centrifugation in one fractionating cycle can be further fractionated in a subsequent fractionating cycle to provide yet another soluble protein fraction. According to an embodiment, the method can include about two to about four fractionating cycles of insoluble protein fractions, thereby providing a plurality of additional soluble protein fractions. The plurality of additional soluble protein fractions can be pooled and added to the original SPF obtained from the original fractionation of the EGS. The soluble protein fraction (SPF) or "Fraction B" can include the pooled soluble protein fractions. The SPF can be used for IP injection in an animal or human for treating diabetes. The SPF (Fraction B) can include lipids as well as soluble proteins (about 87% soluble proteins and about 13% lipids).

The concentration of lipids in the soluble protein fraction can be determined, e.g., by extracting the lipids from a freeze-dried soluble protein fraction and weighing the extracted lipids. If the soluble protein fraction includes about 87% soluble proteins, but less than about 13% lipids, additional lipids can be extracted directly from an EGS and added to the freeze-dried soluble protein fraction to increase the lipid percentage to about 13%. The additional lipids can be extracted from the freeze-dried original EGS. As described in detail, below, lipid extraction can be carried out in the dark and the extracted lipids can be stored under nitrogen until added to the soluble protein fraction. The lipids can be added with an organic solvent, e.g., isopropyl alcohol, to the freeze-dried soluble protein fraction to increase the lipid concentration to about 13% of the total soluble protein-lipid fraction. The organic solvent can be evaporated under vacuum at room temperature.

In an embodiment, if it is determined that the soluble protein fraction includes about 87% soluble proteins but less than about 13% lipids (which is generally the case), additional lipids can be provided by extracting lipids from the EGS with an organic solvent mixture. The additional lipids can be obtained from the freeze-dried EGS by extracting the lipids with an organic solvent mixture including chloroform:methanol:isopropanol (2:1:0.250, v/v) for about 72 hours on a stirring plate. The extracted lipids can then be obtained by filtration, e.g., using a vacuum pump and a Buchner funnel. The lipid extracts can be concentrated to dryness on a rotary evaporator at about 25° C. in the dark and weighed to ensure that the required weight of lipids to be added to the soluble protein fraction is achieved. The required amount of lipids can be dissolved in a suitable organic solvent, e.g., isopropyl alcohol, and added to the soluble freeze-dried protein fraction to increase the lipid fraction in the soluble protein fraction to about 13% of the combined weight of the proteins and lipids. The organic solvent can be evaporated under vacuum at room temperature in the dark to provide a freeze dried soluble protein fraction having about 87% soluble proteins and about 13% lipids of the total combined soluble proteins and lipids. The freeze dried soluble protein fraction (soluble proteins combined with the lipids) can be stored under nitrogen at about −80° C. until needed for injection. The freeze dried soluble fraction can be maintained at about −80° C. (deep freeze) for long-term storage to prevent any unwanted chemical reaction. The enzymes in the fraction will not react against the components in the fraction if kept at about −80° C. during storing for lengthy periods of time under nitrogen. Also the lipids in the soluble protein fraction will be protected from decomposition if kept the same way in deep freeze until required for use. Nitrogen will not allow aerial oxygen to react with the lipids. The SPF is preferably stored in portions appropriate for a single injection at −80° C. It can then be thawed, kept in ice, and administered as needed.

A therapeutically effective amount of the composition including the SPF (Fraction B) can be administered to a patient to treat diabetes. A therapeutically effective amount can include about 3 mg to about 3.5 mg of the SPF (e.g., SPF including about 85% soluble protein and about 13% total lipids) per 100 gm of body weight of the patient (animal or human) to be treated. The therapeutic composition can be administered to a patient in need thereof, preferably by intraperitoneal (IP) or sub-cutaneous (SC) injection after dissolution of the SPF in saline, phosphate buffered saline, or other delivery system, such as nanotechnology delivery systems. The therapeutic composition can be combined with a pharmaceutically acceptable carrier. The therapeutic composition can be administered using other delivery methods, e.g., oral administration, provided that the composition is protected from the digestive effects of the elementary canal for oral administration, such as by encapsulation or nanoparticle technology. Prior to injection of the soluble protein fraction, the freeze-dried soluble fraction can be dissolved in saline or phosphate buffered saline.

As set forth herein, the therapeutic composition including the SPF was administered to STZ-treated male rats as a model for diabetic animals. Treatment of these animals with the SPF composition led to production of natural insulin and reduction of glucose levels.

Accordingly, the SPF (Fraction B) composition can be administered to a patient to treat diabetes. A concentration of 3.0-3.5 mg SPF/kg of human body weight can be administered to a patient or animal in need thereof. Prior to the injection of SPF (SPF Fraction B), the SPF can be dissolved in saline or phosphate buffered saline and sterilized with ultrasound or by passing through a membrane filter.

The SPF (Fraction B) composition can be administered to a patient to treat diabetes, diseases that result from diabetes, or diseases similar in symptoms and caused by other reasons. As used herein, "treating diabetes" can include curing diabetes and repairing damaged organs and tissues affected by diabetes. For example, the SPF (Fraction B) composition can be administered to a patient to treat kidney failure (nephropathy), liver cirrhosis, heart failure, nervous diseases, neuropathy, retinopathy and fertility problems through regeneration of affected organs and tissues.

The SPF is preferably stored in portions appropriate for a single injection at $-80°$ C. It is then thawed, kept in ice and injected as needed.

As described herein, the preparation was injected inter peritoneally (IP) at a concentration of 0.3-0.4 mg protein/ 100 g body weight in non-fasting Sprague-Dawley (SD) rats previously treated with streptozotocin (STZ) to induce diabetes. Reduction of blood glucose to close to normality was achieved in 5 weeks, with once a day injection of the prepared soluble fraction. The level of insulin in the serum of the treated animals showed significant improvement over non-treated diabetic control animals. Histological studies of the pancreas showed recovery of Langerhans Islets (the insulin secreting Islets) compared to the diabetic control non-treated animals and comparable to the non-diabetic control animals. Biochemical studies indicated significant recovery of functions of the kidneys, the liver, and the heart of the treated animals compared to the normal non-diabetic control animals and the diabetic non-treated animals.

A therapeutically effective amount of the SPF can include about 3 mg to about 3.5 mg of the SPF (which includes about 87% soluble protein and about 13% total lipids) per kg of body weight of the animal or human to be treated.

The following examples illustrate the present teachings.

Example 1

Preparation of SPF and Calculation of Soluble Protein in Solution

EGS was collected from the catfish skin and kept at $-80°$ C. until use. Frozen EGS was thawed to $4°$ C., mixed with an equal volume of extraction buffer [phosphate buffered saline (PBS), 0.05 M containing ($NaH_2PO_4/Na_2HPO_4$) and 0.14 M NaCl, pH 7.5], and homogenized with an Ultra Truex (IKA) homogenizer. This step and all subsequent purification procedures were carried out at $4°$ C. unless otherwise indicated. The homogenate was centrifuged at 15,000 rpm for 15 min. The supernatant was collected, and the pellet (insoluble protein etc.) was re-extracted with extraction buffer (2-4 times). Each time, the soluble fraction was separated by centrifugation as described above, and the two extracted fractions were pooled. The combined extracted fractions provided the soluble protein fraction (SPF) (Fraction B).

To find the concentration of catfish soluble proteins in the SPF (Fraction B), the SPF was diluted with PBS (1:50). 0.1 ml of the diluted sample was mixed well with 5 ml of Coomassie Brilliant Blue solution and kept in tubes at room temperature for about 10 minutes. Absorbance was read at 595 nm for the sample, and its protein concentration was determined by comparing its absorbance against absorbance for a standard curve for different bovine serum albumin concentrations. Fraction B was found to include about 85% soluble proteins and about 13% lipids.

The SPF (Fraction B) was then dissolved in the extraction buffer and diluted with saline for injection.

Example 2

Diabetes Treatment

Figure 1B:
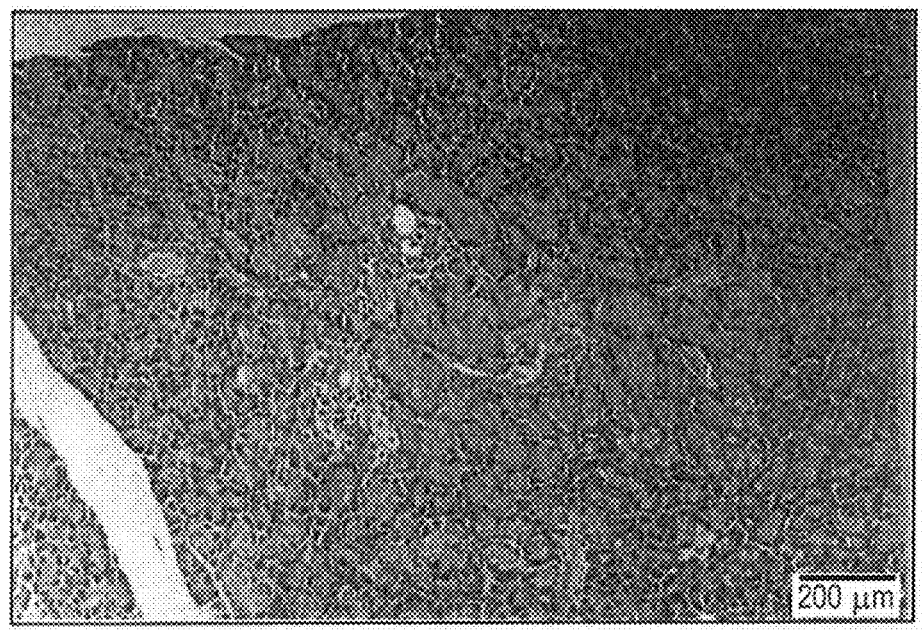
FIG. 1B shows a histological slide of the pancreas of STZ-treated diabetic rats, showing collapsed Langerhans Islets.
Figure 1C:
FIG. 1C shows a histological slide of the pancreas of STZ-treated diabetic rats after once a day IP injection with the therapeutic composition for 8 weeks, showing regenerated Langerhans Islets.
Figure 2:
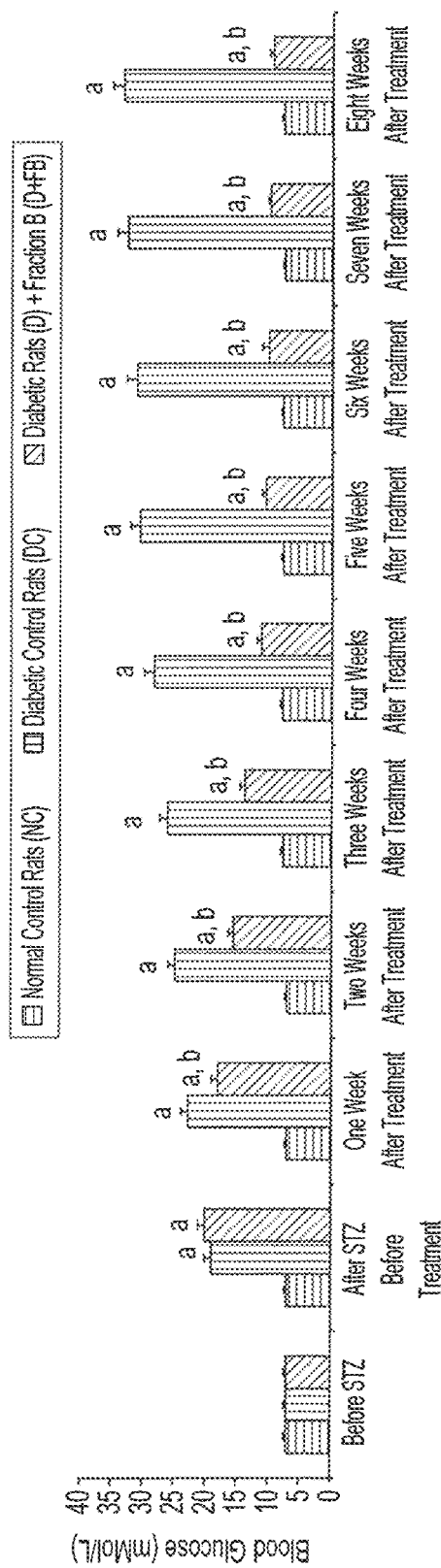
FIG. 2 is a graph showing the effect of the therapeutic composition on blood glucose of STZ-treated diabetic rats.
Figure 3:
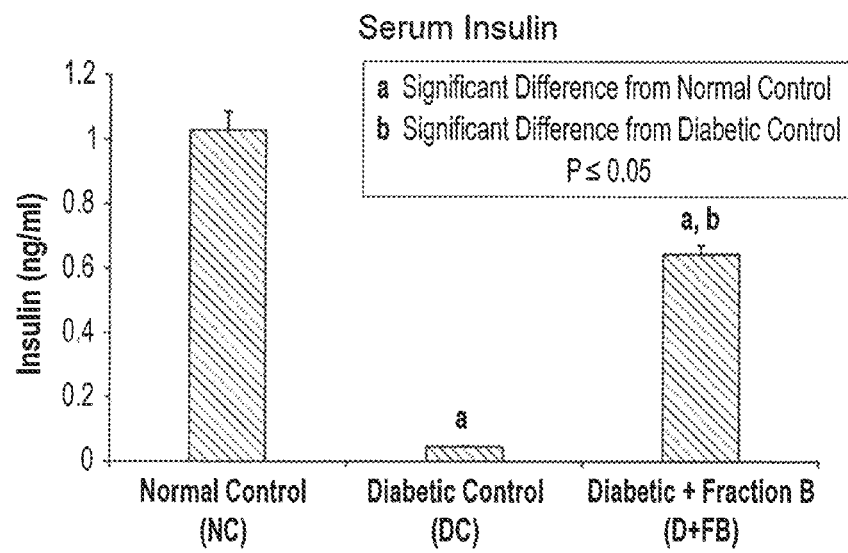
FIG. 3 is a graph showing the effect of the therapeutic composition on serum insulin of STZ-treated diabetic rats after eight weeks of treatment.
Figure 4:
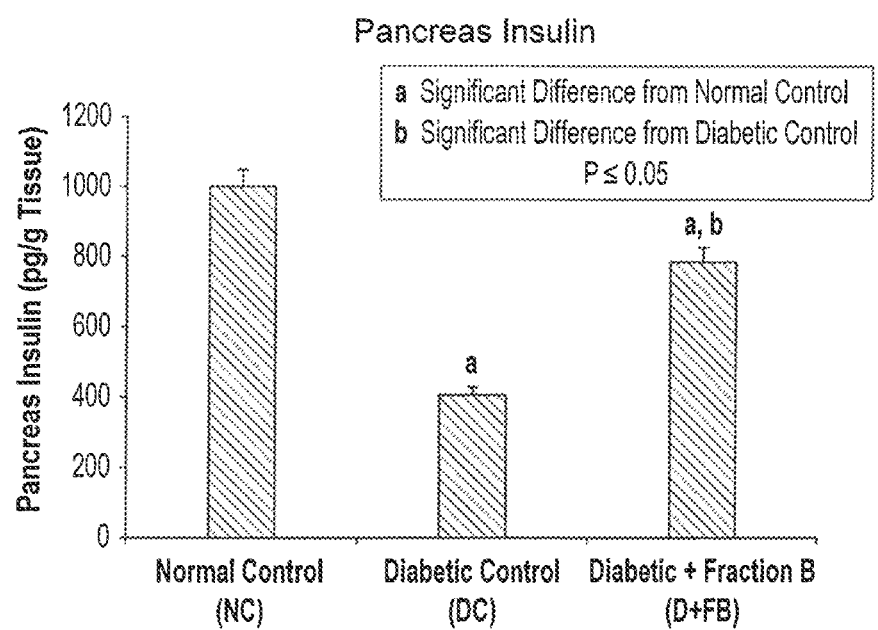
FIG. 4 is a graph showing the effect of the therapeutic composition on pancreas insulin of STZ-treated diabetic rats after eight weeks of treatment.

The SPF (Fraction B) was administered intra-peritoneally to non-fasting Sprague-Dawley (SD) rats (daily dosage of 0.3 mg-0.35 mg SPF/100 g body weight) previously treated with streptozotocin (STZ). This was followed by once a week testing of blood glucose levels over 8 weeks period. Blood glucose levels were measured for diabetic control SD rats and normal non-diabetic control SD rats on the same days as the diabetic treated rats. The glucose level of the treated diabetic rats began to drop starting from the first week of treatment as seen from blood glucose analysis (FIG. 2.) The reduction of glucose in the treated animals continued to drop until the fifth week of treatment, when it became close to the level of blood glucose of normal control animals. Continuation of the treatment for 8 weeks only reduced the glucose level by a small amount. After 8 weeks of daily treatment, the 3 groups of animals were sacrificed after being anaesthetized with ketamine/xylazine (9:1). The insulin levels in the three groups of animals (the normal control, the diabetic non-treated, and the diabetic treated) were measured in their blood serum, as well as in the homogenized pancreas of each of the three groups of animals (FIGS. 3-4, respectively). The pancreas, the kidneys, the heart, and the liver were removed for biochemical and histological studies. The pancreas of the 3 groups of animals were fixed, sectioned and stained for histological studies. The normal, control non-diabetic animals showed well-defined Langerhans Islets, with prominent beta cells (FIG. 1A). The diabetic control, non-treated groups of animals showed only traces of ill-defined structures, which might have been Langerhans Islets (FIG. 1B). Some of the traces of the Islet had a few beta cells. The treated diabetic animals showed clear and well-defined Langerhans Islets with numerous beta cells, indicating regeneration (recovery) of the pancreas (FIG. 1C). Reduction of blood glucose to approximately normal levels was achieved in 5 weeks (FIG. 3). The level of insulin in the serum of the treated animals showed significant improvement over the non-treated diabetic control animals. Biochemical studies indicated significant recovery of kidney, heart, and liver functions, compared to the normal, non-diabetic control animals and the diabetic, non-treated animals.

To find out whether the released insulin in the serum came from the regenerated pancreas of the treated diabetic animals, the pancreas of the three groups of animals (the normal non-diabetic control animals, the diabetic control non-treated animals and the diabetic treated animals) were analyzed for the presence of insulin. The pancreas of the treated diabetic animals showed a concentration of insulin significantly higher than that of the diabetic non-treated animals (FIG. 4). Another confirmatory test to establish that the regenerated Langerhans Islets produced the insulin in the treated diabetic animals included staining the pancreas of the three groups of animals (the normal non-diabetic control animals, the diabetic non-treated control animals and the diabetic treated animals) specifically for the presence of insulin with immunohistochemical staining. The pancreas of the control non-diabetic animals and those of the diabetic, treated animals showed the confirmatory color for insulin, indicating the location of insulin within the Langerhans Islets, while the pancreas of the diabetic non-treated control animals did not show any color for insulin, indicating the lack of Langerhans Islets. Biochemical studies indicated that in the treated diabetic animals, not only the pancreas showed recovery (regeneration), but also significant recovery of the kidneys, the liver and the heart functions were obtained, compared to the normal non-diabetic control animals and the diabetic non-treated control animals. Testes of diabetic non-treated animals were shrunk to a small size after 8 weeks of the animals being diabetic compared to the testes of the normal control animals. The testes of the treated diabetic animals showed significant recovery in their size.

The following biochemical analysis results and other measurements were obtained:

1—Reduction of blood glucose in the treated animals started remarkably from the first week of treatment, and its average in the treated animals reached very close to normal by the end of 5 weeks (FIG. 2).

Figure 5:
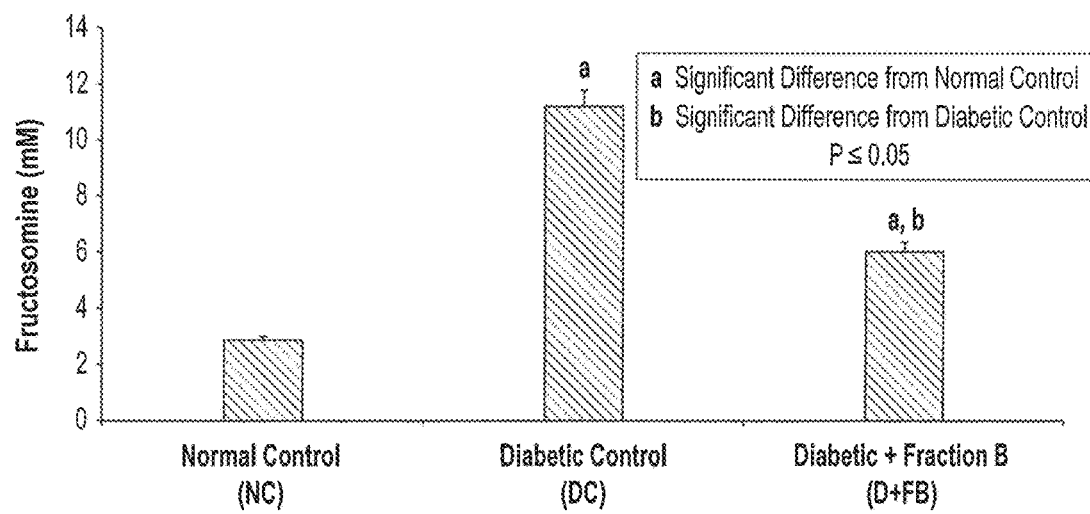
FIG. 5 is a graph showing the effect of the therapeutic composition on serum fructosamine of STZ-treated diabetic rats after eight weeks of treatment.

2—Significant reduction in blood serum fructosamine in the treated diabetic animals compared to control diabetic and non-diabetic control animals was obtained, indicating less glucose was attached to serum proteins during the 8 week period of the trial experiment (FIG. 5).

3—Significant levels of insulin in blood serum and in pancreatic tissues in the treated animals compared to non-treated diabetic animals and non-diabetic control animals was obtained, indicating recovery (regeneration) of the pancreas in the treated diabetic animals (FIGS. 3-4).

Figure 6:
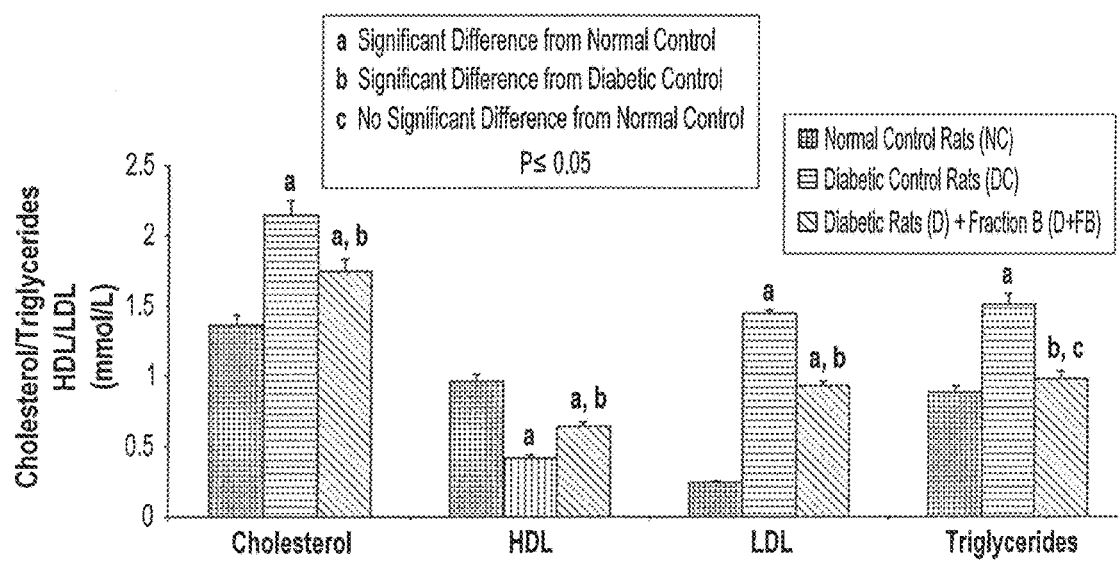
FIG. 6 is a graph showing the effect of the therapeutic composition on pancreas insulin of STZ-treated diabetic rats after eight weeks of treatment.

4—Significant reduction of serum cholesterol, triglycerides, HDL and LDL in the treated diabetic animals compared to control diabetic and non-diabetic control animals was obtained (FIG. 6).

Figure 7:
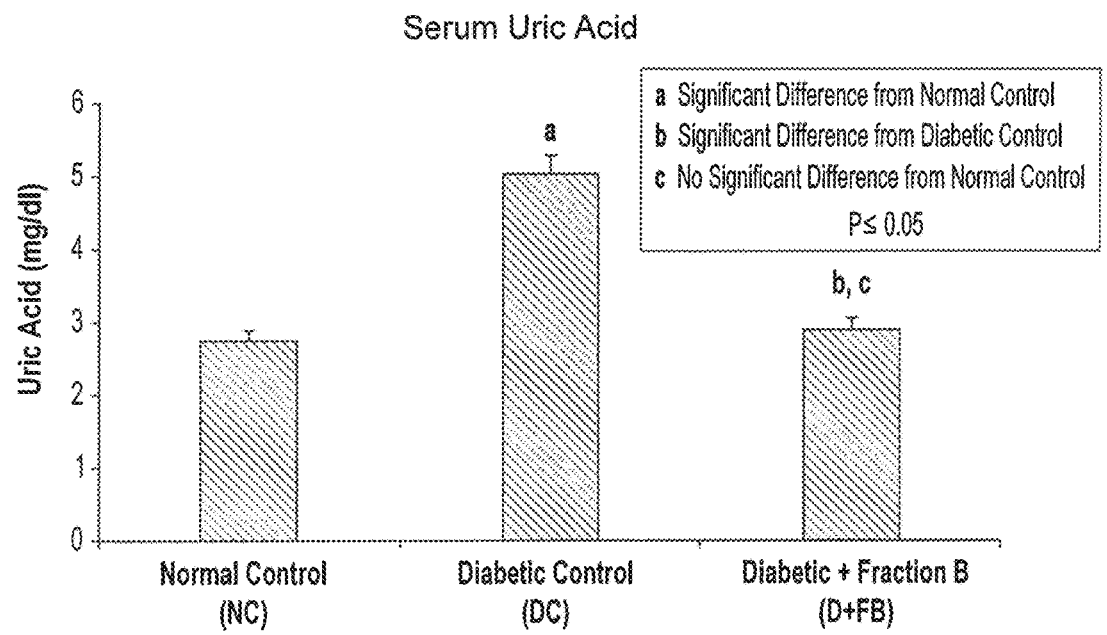
FIG. 7 is a graph showing the effect of the therapeutic composition on serum uric acid of STZ-treated diabetic rats after eight weeks of treatment.
Figure 8:
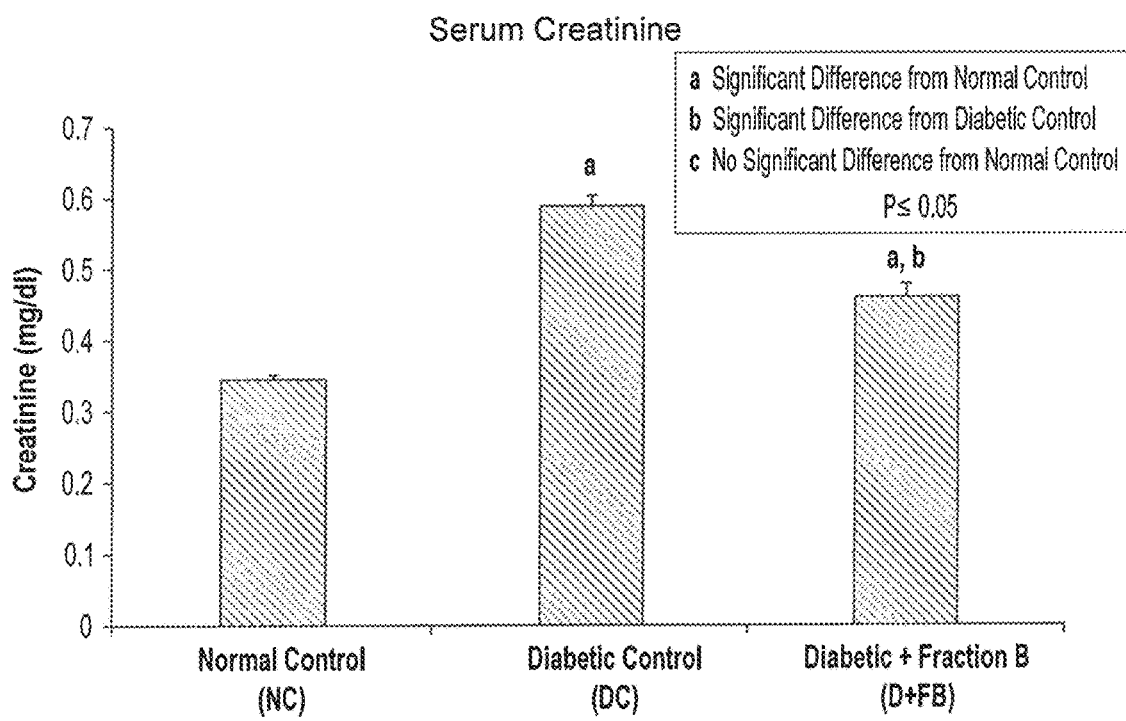
FIG. 8 is a graph showing the effect of the therapeutic composition on serum creatinine of STZ-treated diabetic rats after eight weeks of treatment.

5—Significant reduction of serum uric acid and serum creatinine in the treated diabetic animals compared to control diabetic and non-diabetic control animals was obtained, indicating recovery (regeneration) of the functions of the kidneys (FIGS. 7-8).

Figure 9:
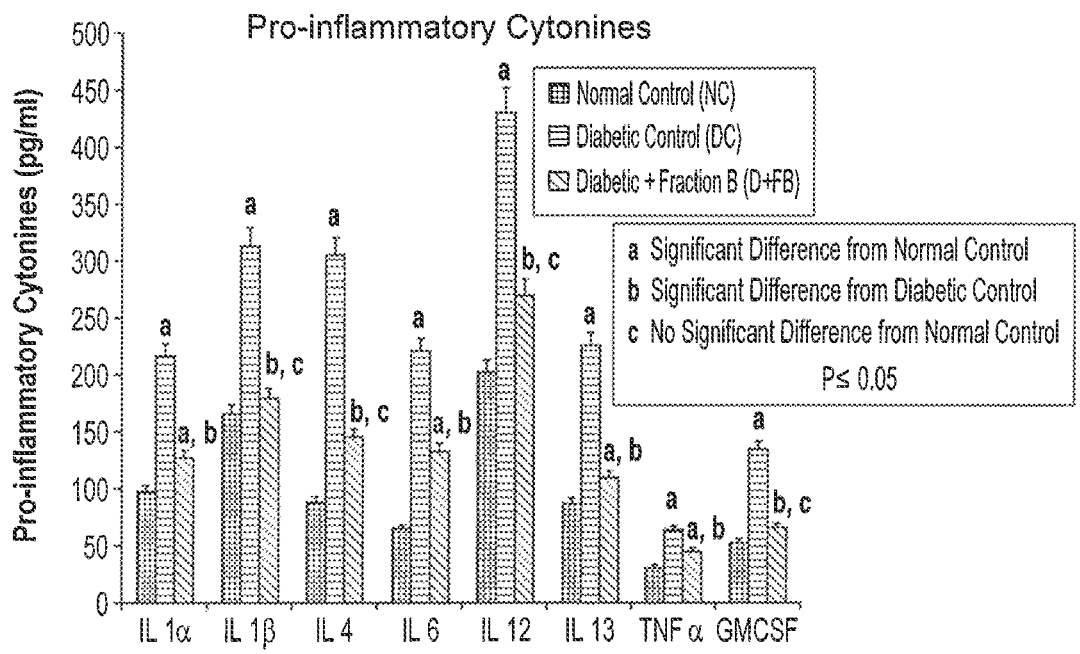
FIG. 9 is a graph showing the effect of the therapeutic composition on serum proinflammatory cytokines of STZ-treated diabetic rats after eight weeks of treatment.
Figure 10:
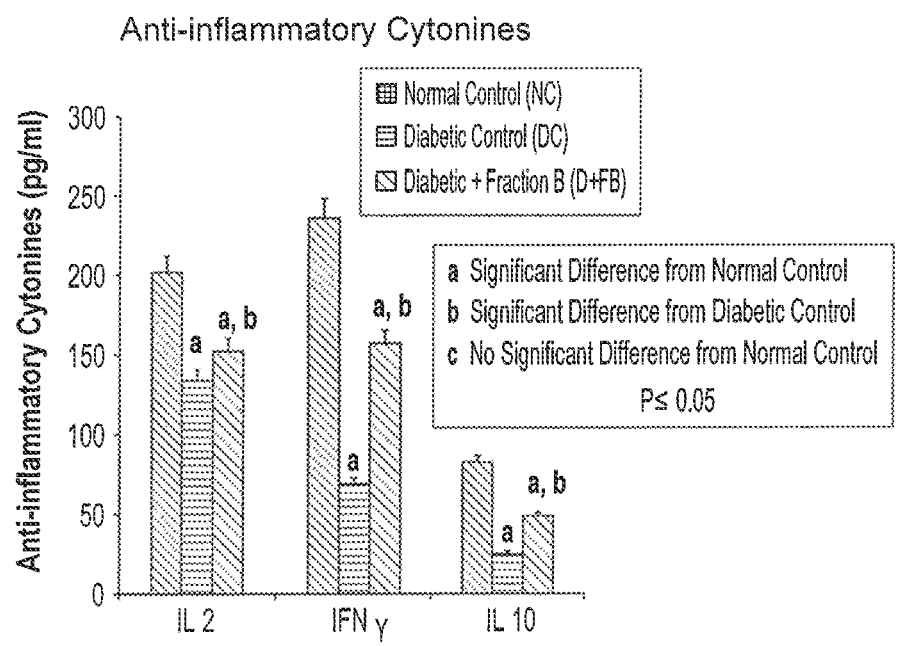
FIG. 10 is a graph showing the effect of the therapeutic composition on serum anti-inflammatory cytokines of STZ-treated diabetic rats after eight weeks of treatment.

6—Significant reduction of serum proinflammatory and increase of anti-inflammatory cytokines in diabetic treated rats compared to the diabetic non-treated rats was observed (FIGS. 9-10).

Figure 11:
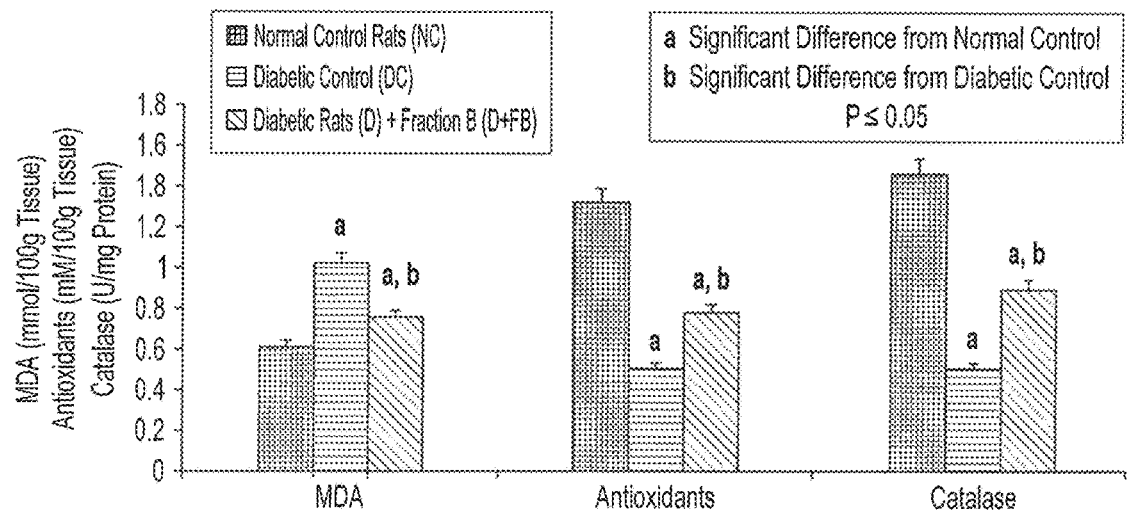
FIG. 11 is a graph showing the effect of the therapeutic composition on liver malondialdehyde (MDA), antioxidants, and catalase of STZ-treated diabetic rats after eight weeks of treatment.

7—Significant increase of liver malondialdehyde (MDA), anti-oxidants and catalase in treated diabetic rats compared to control diabetic and non-diabetic control animals was obtained, indicating recovery (regeneration) of the functions of the liver (FIG. 11).

Figure 12:
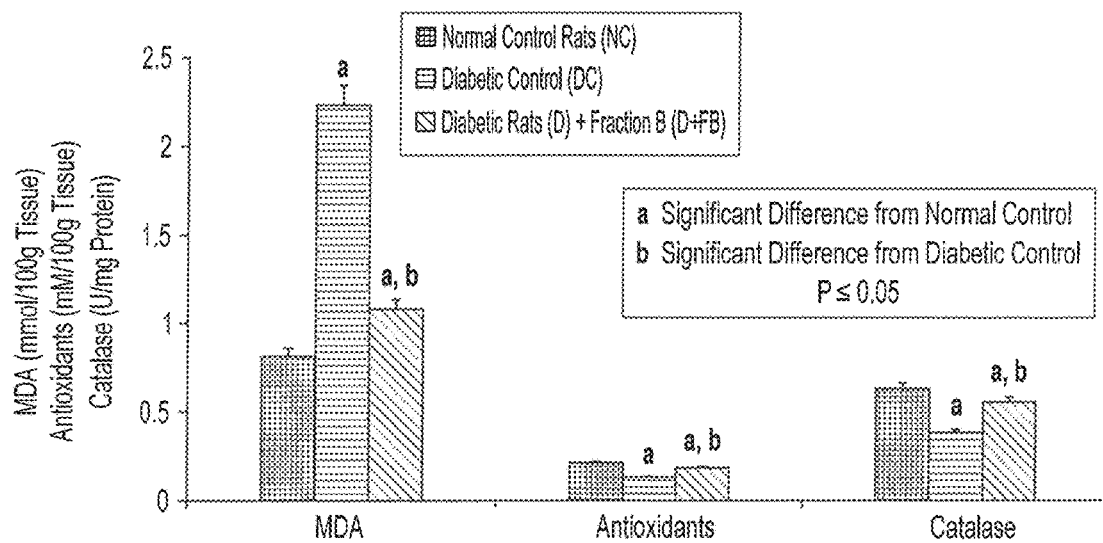
FIG. 12 is a graph showing the effect of the therapeutic composition on kidney malondialdehyde (MDA), antioxidants, and catalase of STZ-treated diabetic rats after eight weeks of treatment.

8—Significant increase of kidney malondialdehyde (MDA), anti-oxidants and catalase in treated diabetic rats compared to control diabetic and non-diabetic control animals was observed, indicating recovery (regeneration) of the functions of the kidney (FIG. 12).

Figure 13:
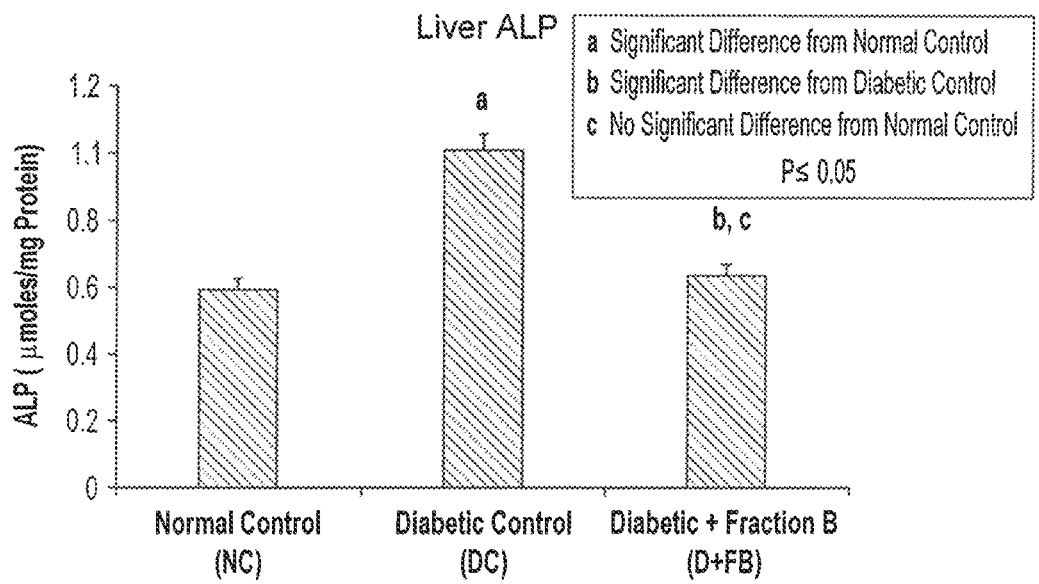
FIG. 13 is a graph showing the effect of the therapeutic composition on liver alkaline phosphatase (ALP) in diabetic rats after eight weeks of treatment.
Figure 14:
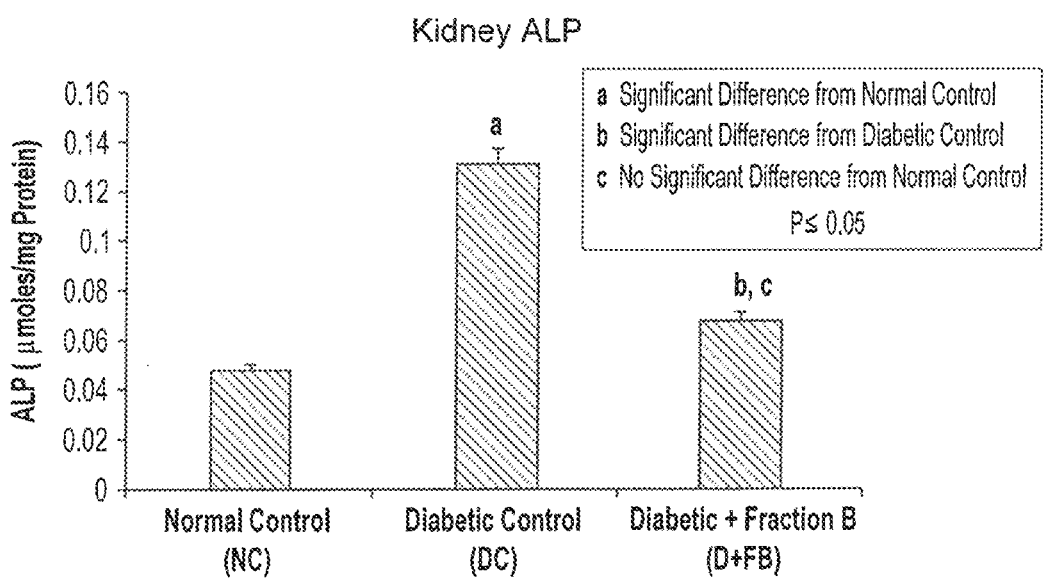
FIG. 14 is a graph showing the effect of the therapeutic composition on kidney alkaline phosphatase (ALP) in diabetic rats after eight weeks of treatment.

9—Significant recovery of liver and kidney alkaline phosphatase (ALP) in treated diabetic animals compared to normal control animals and diabetic control non-diabetic animals was observed, indicating recovery (regeneration) of both liver and kidneys (FIGS. 13-14).

Figure 15:
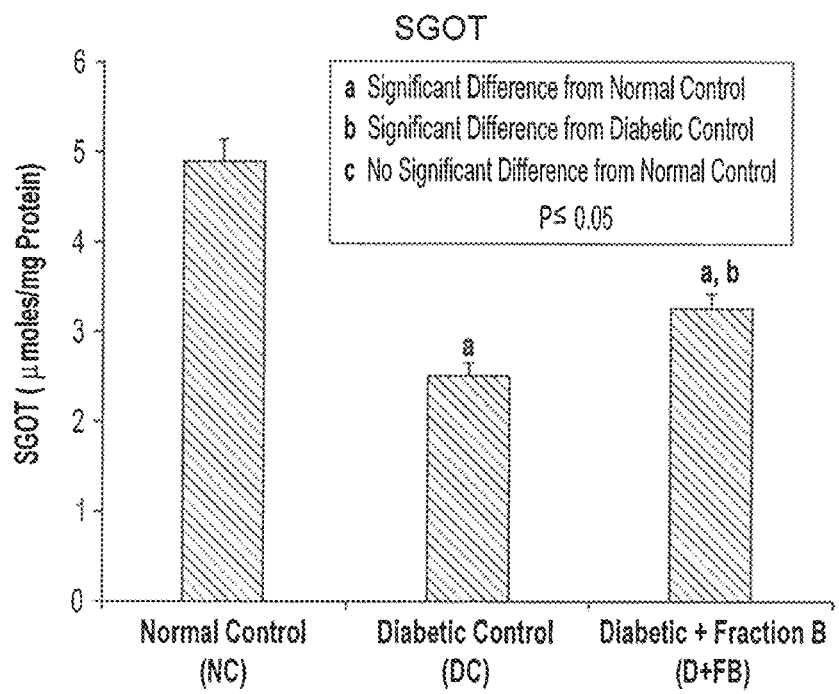
FIG. 15 is a graph showing the effect of the therapeutic composition on heart enzymes (SGOT) of diabetic rats after eight weeks of treatment.
Figure 16:
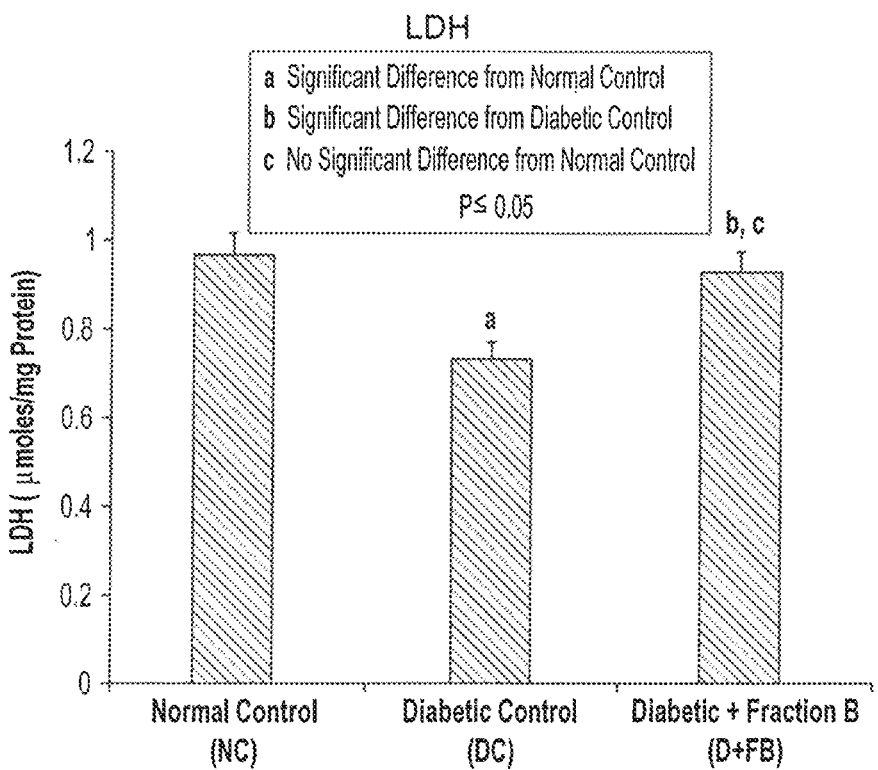
FIG. 16 is a graph showing the effect of the therapeutic composition on heart enzymes (LDH) of diabetic rats after eight weeks of treatment.
Figure 17A:
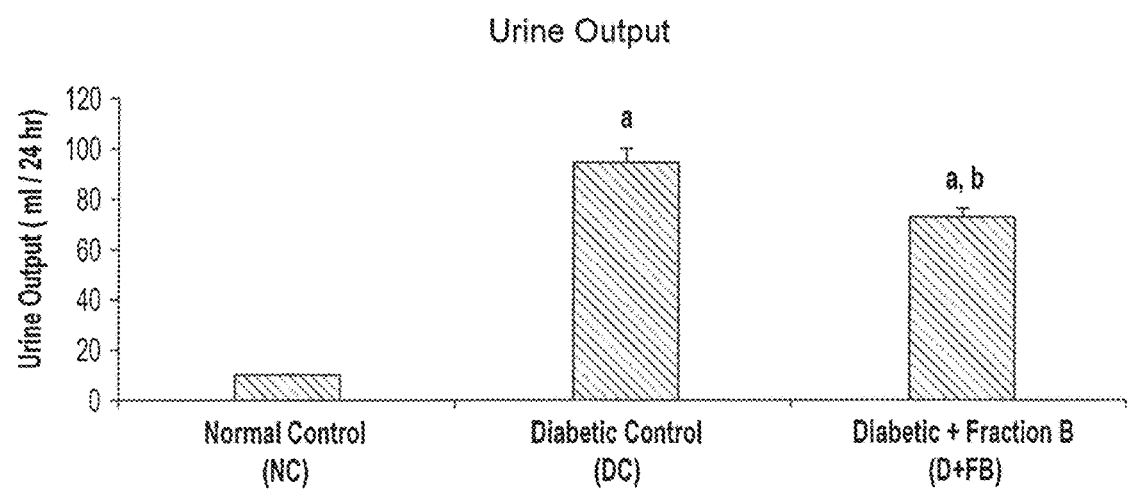
FIG. 17A is a graph showing the effect of the therapeutic composition on urine output of diabetic rats after eight weeks of treatment.
Figure 17B:
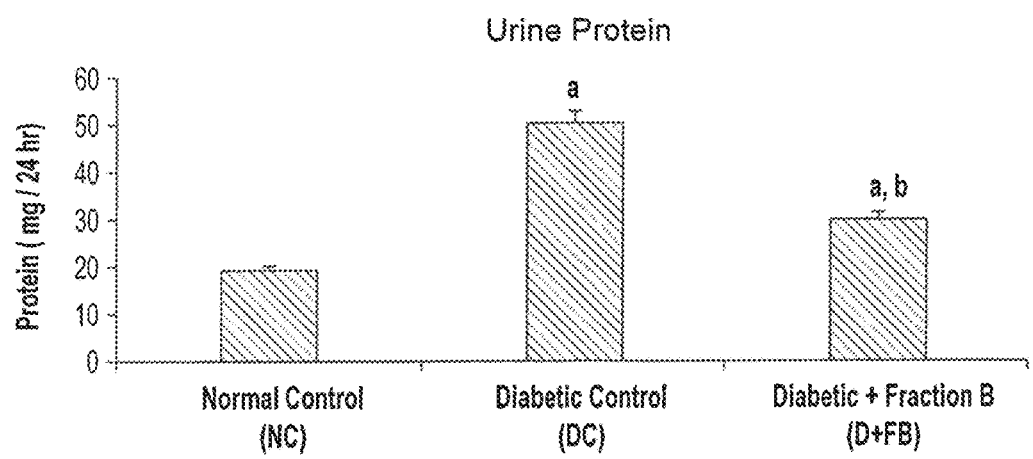
FIG. 17B is a graph showing the effect of the therapeutic composition on urine protein of diabetic rats after eight weeks of treatment.
Figure 17C:
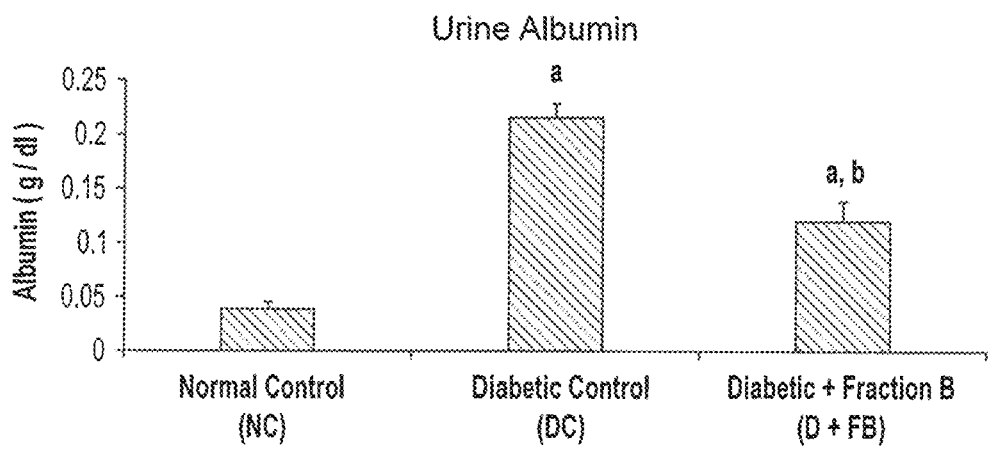
FIG. 17C is a graph showing the effect of the therapeutic composition on urine albumin of diabetic rats after eight weeks of treatment.
Figure 17D:
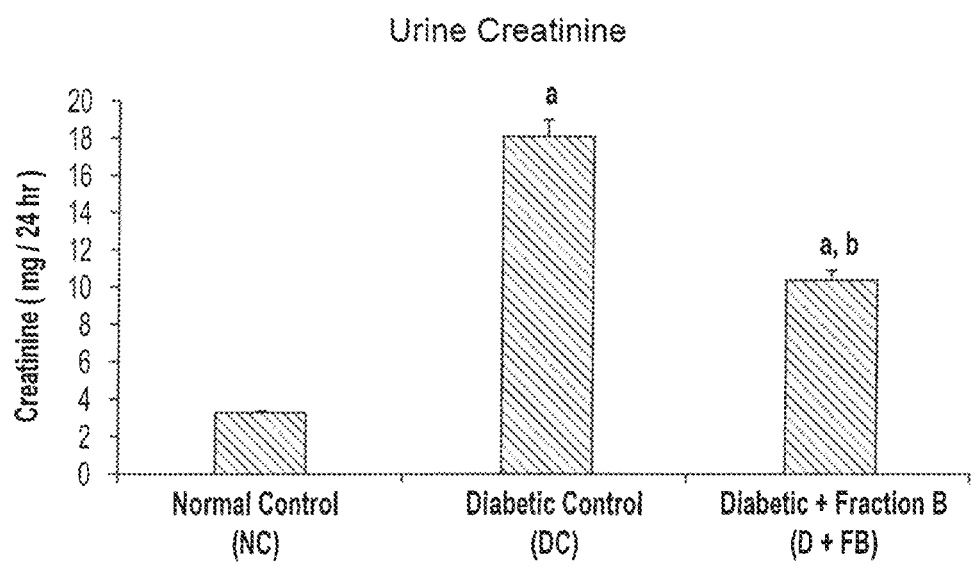
FIG. 17D is a graph showing the effect of the therapeutic composition on urine creatinine of diabetic rats after eight weeks of treatment.
Figure 17E:
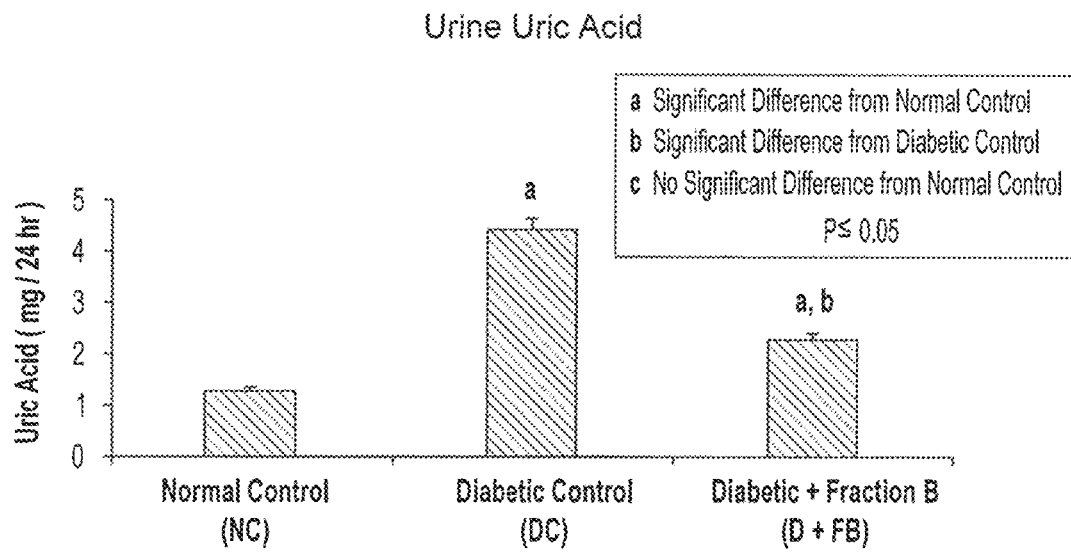
FIG. 17E is a graph showing the effect of the therapeutic composition on urine uric acid of diabetic rats after eight weeks of treatment.

10—Significant recovery of heart enzymes (SGOT and LDH) in treated diabetic animals compared to diabetic non-treated animals and normal non-diabetic animals was observed, indicating recovery of heart functions (regeneration) (FIGS. 15-16).

11—Significant changes in urine parameters (urine output. Urine protein, urine albumin, urine creatinine and urine uric acid) was observed, indicating recovery (regeneration) of the functions of the kidney (FIGS. 17A-17E).

Figure 18:
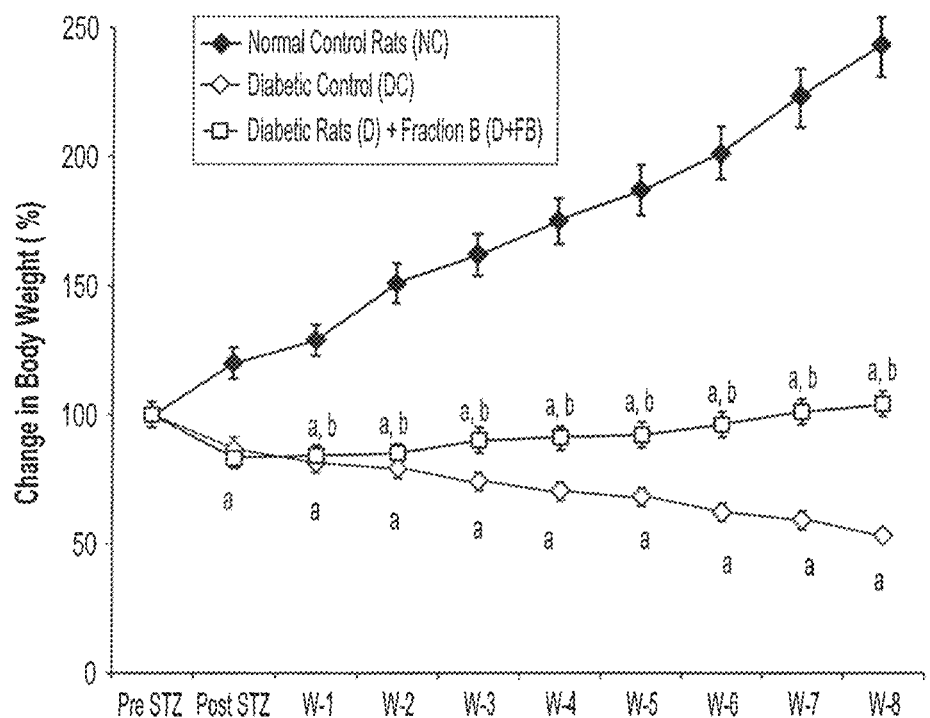
FIG. 18 is a graph showing the effect of the therapeutic composition on body weight of diabetic rats after eight weeks of treatment.

12—Significant body weight % recovery in diabetic treated animals compared to normal non-diabetic animals and diabetic non-treated animals was observed, indicating regeneration of organs and tissues that have been damaged by diabetes and STZ and improvement of metabolism of body functions in treated diabetic animals (FIG. 18).

Figure 19:
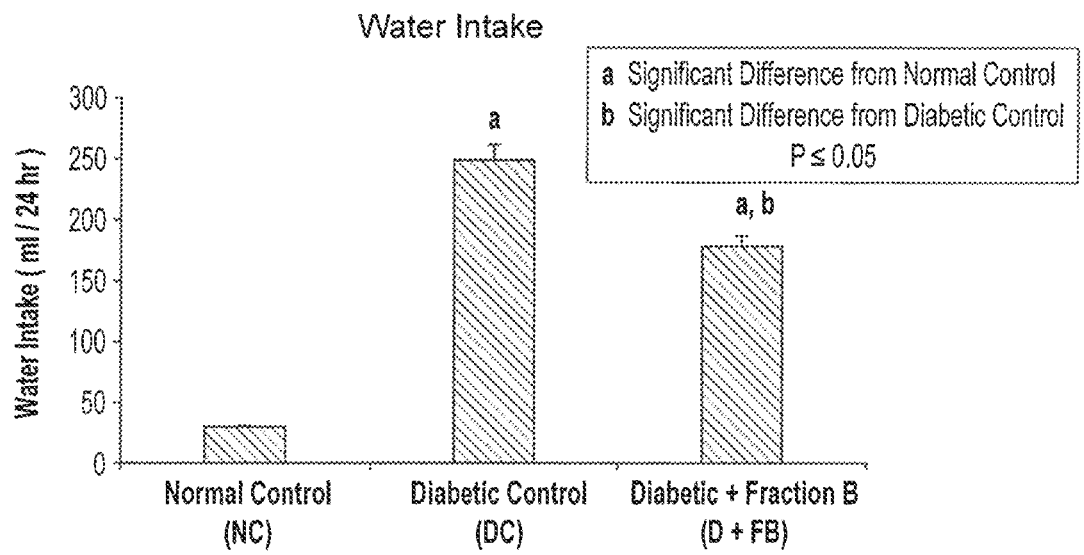
FIG. 19 is a graph showing the effect of the therapeutic composition on water intake of diabetic rats after eight weeks of treatment.
Figure 20:
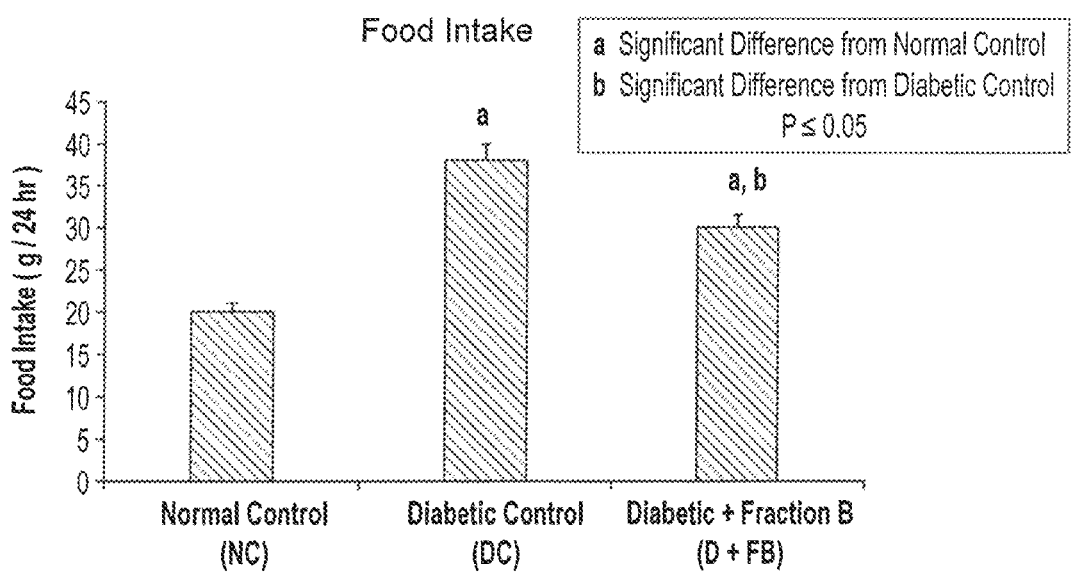
FIG. 20 is a graph showing the effect of the therapeutic composition on water intake of diabetic rats after eight weeks of treatment.

13—Significant improvement in water and food intake by diabetic treated animals compared to non-diabetic control animals and diabetic non-treated control animals was observed (FIGS. 19-20).

14—The testes showed remarkable recovery in its size in the treated diabetic rats compared to the normal non-diabetic rats and diabetic control rats.

15—Laboratory test results for blood chemistry and CBC for mice treated with SPF for Pane-1 cell tumor were comparable to those of normal control mice, indicating that the material is not toxic to the blood [benign].

16—Treatment with the therapeutic composition can also be applied to diseases similar to those described and result from diabetes, such as kidney failure (nephropathy), liver cirrhosis, heart failure, retinopathy and fertility problems.

Reduction of blood glucose in the treated animals started remarkably from the first week of treatment, and its average in the treated animals reached very close to normal by the end of 8 weeks. Significant levels of insulin in the treated animals was observed, indicating recovery of the pancreas in the treated diabetic animals compared to control diabetic and non-diabetic control animals. Significant reduction in serum cholesterol in the treated diabetic animals compared to control diabetic and non-diabetic control animals was observed. Significant reduction in serum fructosamine in the treated diabetic animals compared to control diabetic and non-diabetic control animals was observed, indicating less sugar attached to serum proteins during the 8 week period of the trial experiment. Significant reduction in serum creatinine in the treated diabetic animals compared to control diabetic and non-diabetic control animals was observed, indicating significant improvement in kidney functions. Significant reduction in urine creatinine in the treated diabetic animals compared to control diabetic and non-diabetic control animals was observed. Kidney malondialdehyde (MDA) was significantly reduced in kidneys of the treated diabetic animals compared to control diabetic and non-diabetic control animals, indicating significant improvement in kidney functions. Liver malondialdehyde (MDA) was significantly reduced in the treated diabetic animals compared to control diabetic and non-diabetic control animals, indicating significant improvement in liver functions. Significant increase in kidney catalase (anti-oxidant enzyme) in the treated diabetic animals compared to control diabetic and non-diabetic control animals indicated significant improvement in kidney functions. Liver catalase was significantly increased in the treated diabetic animals compared to control diabetic and non-diabetic control animals, indicating significant improvement in liver functions. Significant increase in kidney antioxidants in the treated diabetic animals compared to control diabetic and non-diabetic control animals indicated significant improvement in kidney functions. Significant increase in liver antioxidants in the treated diabetic animals compared to control diabetic and non-diabetic control animals indicated significant improvement in liver functions. Significant decrease in serum triglycerides in the diabetic treated animals compared to the control non-diabetic and the control diabetic animals was observed. Significant reduction in proinflammatory markers in the treated diabetic animals compared to the other 2 groups was observed. Heart lactate dehydrogenase (LDH) levels in diabetic rats treated with the SPF (fraction B) were close to those of the normal control rats and significantly different from the untreated or control diabetic rats. The LDH levels for the diabetic control rats were significantly different from the normal control rats. The results of biochemical analysis of, blood serum, urine, and other biochemical analysis results of the 3 groups of animals (the normal control, the diabetic control and the treated diabetic animals) are summarized in Tables 1-64 below.

TABLE 1

Effect of Fraction B on Serum Interleukin I Alpha (IL 1α) in Diabetic Rats

| GROUP NAME | IL 1α (pg/ml) |
|---|---|
| NORMAL CONTROL (NC) | 97.71 ± 5.33 |
| DIABETIC CONTROL (DC) | 215.97 ± 12.24 |
| DIABETIC + FRACTION B (D + FB) | 127.49 ± 6.038 |

TABLE 2

Significance Levels for Table 1

| GROUP NAME | SIGNIFICANCE LEVEL |
|---|---|
| NC vs. DC | 0.004 |
| DC vs. D + FB | 0.015 |
| NC vs. D + FB | 0.035 |

TABLE 3

Effect of Fraction B on Serum Interleukin I Beta (IL 1β) in Diabetic Rats

| GROUP NAME | IL 1β (pg/ml) |
|---|---|
| NORMAL CONTROL (NC) | 165.25 ± 10.33 |
| DIABETIC CONTROL (DC) | 314.31 ± 13.39 |
| DIABETIC + FRACTION B (D + FB) | 179.18 ± 8.038 |

TABLE 4

Significance Levels for Table 3

| GROUP NAME | SIGNIFICANCE LEVEL |
|---|---|
| NC vs. DC | 0.014 |
| DC vs. D + FB | 0.020 |
| NC vs. D + FB | 0.758 |

TABLE 5

Effect of Fraction B on Serum Interleukin 2 (1L 2) in Diabetic Rats

| GROUP NAME | 1L 2 (pg/ml) |
|---|---|
| NORMAL CONTROL (NC) | 202.25 ± 9.37 |
| DIABETIC CONTROL (DC) | 134.43 ± 4.39 |
| DIABETIC + FRACTION B (D + FB) | 152.93 ± 4.038 |

TABLE 6

Significance Levels for Table 5

| GROUP NAME | SIGNIFICANCE LEVEL |
|---|---|
| NC vs. DC | 0.000 |
| DC vs. D + FB | 0.042 |
| NC vs. D + FB | 0.009 |

TABLE 7

Effect of Fraction B on Serum Interleukin 4 (1L 4) in Diabetic Rats

| GROUP NAME | 1L 4 (pg/ml) |
|---|---|
| NORMAL CONTROL (NC) | 89.50 ± 2.68 |
| DIABETIC CONTROL (DC) | 306.08 ± 8.39 |
| DIABETIC + FRACTION B (D + FB) | 146.51 ± 3.39 |

TABLE 8

Significance Levels for Table 7

| GROUP NAME | SIGNIFICANCE LEVEL |
|---|---|
| NC vs. DC | 0.002 |
| DC vs. D + FB | 0.007 |
| NC vs. D + FB | 0.202 |

TABLE 9

Effect of Fraction B on Serum Interleukin 12 (1L 12) in Diabetic Rats

| GROUP NAME | 1L 12 (pg/ml) |
|---|---|
| NORMAL CONTROL (NC) | 204.28 ± 8.19 |
| DIABETIC CONTROL (DC) | 432.00 ± 10.40 |
| DIABETIC + FRACTION B (D + FB) | 272.22 ± 6.52 |

TABLE 10

Significance Levels for Table 9

| GROUP NAME | SIGNIFICANCE LEVEL |
|---|---|
| NC vs. DC | 0.002 |
| DC vs. D + FB | 0.008 |
| NC vs. D + FB | 0.153 |

TABLE 11

Effect of Fraction B on Serum Interleukin 13 (1L 13) in Diabetic Rats

| GROUP NAME | 1L 13 (pg/ml) |
|---|---|
| NORMAL CONTROL (NC) | 89.83 ± 9.59 |
| DIABETIC CONTROL (DC) | 227.99 ± 10.40 |
| DIABETIC + FRACTION B (D + FB) | 112.80 ± 10.52 |

TABLE 12

Significance Levels for Table 11

| GROUP NAME | SIGNIFICANCE LEVEL |
|---|---|
| NC vs. DC | 0.001 |
| DC vs. D + FB | 0.002 |
| NC vs. D + FB | 0.029 |

TABLE 13

Effect of Fraction B on Serum Interferonγ (IFNγ) in Diabetic Rats

| GROUP NAME | IFNγ (pg/ml) |
|---|---|
| NORMAL CONTROL (NC) | 237.02 ± 5.19 |
| DIABETIC CONTROL (DC) | 70.29 ± 1.46 |
| DIABETIC + FRACTION B (D + FB) | 158.32 ± 11.68 |

TABLE 14

Significance Levels for Table 13

| GROUP NAME | SIGNIFICANCE LEVEL |
|---|---|
| NC vs. DC | 0.002 |
| DC vs. D + FB | 0.035 |
| NC vs. D + FB | 0.024 |

TABLE 15

Effect of Fraction B on Serum Tumor Necrosis Factor α (TNFα) in Diabetic Rats

| GROUP NAME | TNFα (pg/ml) |
|---|---|
| NORMAL CONTROL (NC) | 35.02 ± 1.14 |
| DIABETIC CONTROL (DC) | 67.74 ± 1.05 |
| DIABETIC + FRACTION B (D + FB) | 49.53 ± 2.68 |

TABLE 16

Significance Levels for Table 15

| GROUP NAME | SIGNIFICANCE LEVEL |
|---|---|
| NC vs. DC | 0.000 |
| DC vs. D + FB | 0.004 |
| NC vs. D + FB | 0.011 |

TABLE 17

Effect of Fraction B on Granulocyte Macrophage Colony Stimulating (GMCSF) in Diabetic Rats

| GROUP NAME | GMCSF (pg/ml) |
|---|---|
| NORMAL CONTROL (NC) | 56.99 ± 2.14 |
| DIABETIC CONTROL (DC) | 138.47 ± 3.09 |
| DIABETIC + FRACTION B (D + FB) | 70.38 ± 5.68 |

TABLE 18

Significance Levels for Table 17

| GROUP NAME | SIGNIFICANCE LEVEL |
|---|---|
| NC vs. DC | 0.014 |
| DC vs. D + FB | 0.043 |
| NC vs. D + FB | 0.047 |

TABLE 19

Effect of Fraction B on Regulated on activation, normal T Cell Expressed and Secreted (Rantes) in Diabetic Rats

| GROUP NAME | RANTES (pg/ml) |
|---|---|
| NORMAL CONTROL (NC) | 1218.66 ± 159.14 |
| DIABETIC CONTROL (DC) | 2986.01 ± 265.09 |
| DIABETIC + FRACTION B (D + FB) | 1985.38 ± 267.68 |

TABLE 20

Significance Levels for Table 19

| GROUP NAME | SIGNIFICANCE LEVELS |
|---|---|
| NC vs. DC | 0.000 |
| DC vs. D + FB | 0.034 |
| NC vs. D + FB | 0.019 |

TABLE 21

Effect of Fraction B on Serum Insulin in Diabetic Rats after 8 Weeks of Treatment

| GROUP NAME | INSULIN (ng/ml) | % Insulin |
|---|---|---|
| NORMAL CONTROL RATS (NC) | 1.036 ± 0.158 | 100% |
| DIABETIC CONTROL RATS (DC) | 0.052 ± 0.002 [a] | 6% i.e., 94% reduction |
| DIABETIC RATS (D) + FRACTION B (D + FB) | 0.652 ± 0.080 [a, b] | 63%, i.e., 37% reduction |

[a] significant difference from normal control
[b] significant difference from diabetic

TABLE 22

Significance Levels for Table 21

| GROUP NAME | SIGNIFICANCE LEVEL |
|---|---|
| NC vs. DC | 0.000 |
| DC vs. D + FB | 0.000 |
| NC vs. D + FB | 0.009 |

TABLE 23

Effect of Fraction B On Pancreas Insulin in Diabetic Rats After 8 Weeks of Treatment

| GROUP NAME | Pancrease insulin ((pg/g tissue) | % Pancrease insulin |
|---|---|---|
| NORMAL CONTROL (NC) | 1003.87 ± 4.634 | 100% |
| DIABETIC CONTROL (DC) | 409.61 ± 1.213 $^a$ | 40%, ie 60% reduction |
| DIABETIC + FRACTION B (D + FB) | 794.63 ± 3.401 $^{a,\ b}$ | 79%, ie, 21% reduction |

$^a$ significant difference from normal control
$^b$ significant difference from diabetic control

TABLE 24

Significance Levels for Table 23

| GROUP NAME | SIGNIFICANCE LEVEL |
|---|---|
| NC Vs DC | 0.000 |
| DC Vs D + FB | 0.000 |
| NC Vs D + FB | 0.023 |

TABLE 25

Effect Of Fraction B On Serum Fructosamine In Diabetic Rats After 8 Weeks of Treatment

| GROUP NAME | FRUCTOSAMINE (mM) | % FRUCTOSAMINE |
|---|---|---|
| NORMAL CONTROL RATS (NC) | 2.90 ± 0.712 | 100% |
| DIABETIC CONTROL RATS (DC) | 11.36 ± 0.698 $^a$ | 291% increase above normal |
| DIABETIC RATS + FRACTION B (D + FB) | 6.25 ± 0.457 $^{a,\ b}$ | 115% increase above normal |

$^a$ significant difference from normal control
$^b$ significant difference from diabetic control

TABLE 26

Significance Levels for Table 25

| GROUP NAME | SIGNIFICANCE LEVEL |
|---|---|
| NC Vs DC | 0.000 |
| DC Vs D + FB | 0.000 |
| NC Vs D + FB | 0.001 |

TABLE 27

Effect of Fraction B on Serum Cholesterol on Diabetic Rats After 8 Weeks of Treatment

| GROUP NAME | Cholesterol (mmol/l) | % CHOLESTEROL |
|---|---|---|
| NORMAL CONTROL RATS (NC) | 1.36 ± 0.108 | 100% |
| DIABETIC CONTROL RATS (DC) | 2.14 ± 0.122 $^a$ | 57% increase above normal control |
| DIABETIC RATS (D) + FRACTION B (D + FB) | 1.74 ± 0.087 $^{a,\ b}$ | 28% increase above normal control |

$^a$ significant difference from normal control
$^b$ significant difference from diabetic control

TABLE 28

Significance Levels for Table 27

| GROUP NAME | SIGNIFICANCE LEVEL |
|---|---|
| NC Vs DC | 0.018 |
| DC Vs D + FB | 0.038 |
| NC Vs D + FB | 0.023 |

TABLE 29

EFFECT OF FRACTION B ON SERUM HDL IN DIABETIC RATS AFTER 8 WEEKS OF TREATMENT

| GROUP NAME | HDL (mmol/l) | % HDL |
|---|---|---|
| NORMAL CONTROL (NC) | 0.95 ± 0.077 | 100% |
| DIABETIC CONTROL (DC) | 0.41 ± 0.030 $^a$ | 43% i.e., 57% decrease |
| DIABETIC + FRACTION B (D + FB) | 0.63 ± 0.022 $^{a,\ b}$ | 66% i.e., 34% decrease |

$^a$ significant difference from normal control
$^b$ significant difference from diabetic control
$^c$ no significant difference from normal control?

TABLE 30

Significance Levels for Table 29

| GROUP NAME | SIGNIFICANCE LEVEL |
|---|---|
| NC Vs DC | 0.018 |
| DC Vs D + FB | 0.038 |
| NC Vs D + FB | 0.023 |

TABLE 31

Effect Of Fraction B On Serum Uric Acid In Diabetic Rats After 8 Weeks Of Treatment

| GROUP NAME | Serum uric acid (mg/dl) | % Serum uric acid |
|---|---|---|
| NORMAL CONTROL RATS (NC) | 2.79 ± 0.606 | 100% |
| DIABETIC CONTROL RATS (DC) | 5.08 ± 0.663 $^a$ | 82% increase above normal |
| DIABETIC RATS (D) + FRACTION B (D + FB) | 3.02 ± 0.758 $^{b,\ c}$ | 8% increase above normal |

$^a$ significant difference from normal control
$^b$ significant difference from diabetic control
$^c$ no significant difference from normal control?

TABLE 32

Significance Levels for Table 31

| GROUP NAME | SIGNIFICANCE LEVEL |
|---|---|
| NC Vs DC | 0.008 |
| DC Vs D + FB | 0.002 |
| NC Vs D + FB | 0.213 |

TABLE 33

Effect Of Fraction B On Serum Creatinine in Diabetic Rats After 8 Weeks Of Treatment

| GROUP NAME | CREATININE (mg/dl) | % CREATININE |
|---|---|---|
| NORMAL CONTROL RATS (NC) | 0.347 ± 0.023 | 100% |
| DIABETIC CONTROL RATS (DC) | 0.590 ± 0.024 [a] | 70% increase above normal |
| DIABETIC RATS (D) + FRACTION B (D + FB) | 0.460 ± 0.015 [a, b] | 23% increase above normal |

[a] significant difference from normal control
[b] significant difference from diabetic control

TABLE 34

Significance Levels for Table 33

| GROUP NAME | SIGNIFICANCE LEVEL |
|---|---|
| NC Vs DC | 0.000 |
| DC Vs D + FB | 0.001 |
| NC Vs D + FB | 0.002 |

TABLE 35

Effect Of Fraction B On Serum INTERLEUKIN 6 (IL 6; pro-inflamatory) in Diabetic Rats After 8 Weeks Of Treatment

| GROUP NAME | Serum IL 6 ((pg/ml) | % IL 6 |
|---|---|---|
| NORMAL CONTROL RATS (NC) | 66.87 ± 1.034 | 100% |
| DIABETIC CONTROL RATS (DC) | 222.61 ± 1.013 [a] | 234% increase above normal |
| DIABETIC RATS (D) + FRACTION B (D + FB) | 134.63 ± 2.101 [a,b] | 101% increase above normal |

[a] significant difference from normal control
[b] significant difference from diabetic

TABLE 36

Significance Levels for Table 35

| GROUP NAME | SIGNIFICANCE LEVEL |
|---|---|
| NC Vs DC | 0.000 |
| DC Vs D + FB | 0.000 |
| NC Vs D + FB | 0.003 |

TABLE 37

Effect Of Fraction B On Serum INTERLEUKIN 10 (IL 10; anti-inflammatory) in Diabetic Rats After 8 Weeks Of Treatment

| GROUP NAME | Serum IL 10 ((pg/ml) | % IL 10 |
|---|---|---|
| NORMAL CONTROL RATS (NC) | 83.85 ± 0.854 | 100% |
| DIABETIC CONTROL RATS (DC) | 27.18 ± 0.934 [a] | 32%; 68% reduction |
| DIABETIC RATS (D) + FRACTION B (D + FB) | 50.69 ± 1.101 [a,b] | 60%; 40% reduction |

[a] significant difference from normal control
[b] significant difference from diabetic

TABLE 38

Significance Levels for Table 37

| GROUP NAME | SIGNIFICANCE LEVEL |
|---|---|
| NC Vs DC | 0.000 |
| DC Vs D + FB | 0.000 |
| NC Vs D + FB | 0.003 |

TABLE 39

Effect Of Fraction B On Serum Liver MDA (MALONDIALDEHYDE) in Diabetic Rats After 8 Weeks Of Treatment

| GROUP NAME | MDA (mmol/100 g tissue) | % MDA |
|---|---|---|
| NORMAL CONTROL RATS (NC) | 0.608 ± 0.043 | 100% |
| DIABETIC CONTROL RATS (DC) | 1.02 ± 0.037 [a] | 68% increase above normal |
| DIABETIC RATS (D) + FRACTION B (D + PE) | 0.752 ± 0.026 [a,b] | 24% increase above normal |

[a] significant difference from normal control
[b] significant difference from diabetic

TABLE 40

Significance Levels for Table 39

| GROUP NAME | SIGNIFICANCE LEVEL |
|---|---|
| NC Vs DC | 0.000 |
| DC Vs D + FB | 0.000 |
| NC Vs D + FB | 0.021 |

TABLE 41

Effect Of Fraction B On Serum Liver ANTIOXIDANTS in Diabetic Rats After 8 Weeks Of Treatment

| GROUP NAME | LIVER ANTIOXIDANTS (mM/g tissue) | % ANTIOXIDANTS |
|---|---|---|
| NORMAL CONTROL RATS (NC) | 1.32 ± 0.028 | 100% |
| DIABETIC CONTROL RATS (DC) | 0.504 ± 0.032 [a] | 61% ie 39% reduction |
| DIABETIC RATS (D) + FRACTION B (D + FB) | 0.778 ± 0.031 [a,b] | 75% ie 25% reduction |

[a] significant difference from normal control
[b] significant difference from diabetic

TABLE 42

Significance Levels for Table 41

| GROUP NAME | SIGNIFICANCE LEVEL |
|---|---|
| NC Vs DC | 0.000 |
| DC Vs D + FB | 0.001 |
| NC Vs D + FB | 0.008 |

TABLE 43

Effect Of Fraction B On Serum Liver Antioxidants in Diabetic Rats After 8 Weeks Of Treatment

| GROUP NAME | CATALASE (U/mg protein) | % CATALASE |
|---|---|---|
| NORMAL CONTROL RATS (NC) | 1.46 ± 0.063 | 100% |
| DIABETIC CONTROL RATS (DC) | 0.507 ± 0.039 [a] | 34% ie 66% reduction |
| DIABETIC RATS (D) + FRACTION B (D + FB) | 0.890 ± 0.092 [a,b] | 61% ie 39% reduction |

[a] significant difference from normal control
[b] significant difference from diabetic

TABLE 44

Significance Levels for Table 43

| GROUP NAME | SIGNIFICANCE LEVEL |
|---|---|
| NC Vs DC | 0.000 |
| DC Vs D + FB | 0.001 |
| NC Vs D + FB | 0.002 |

TABLE 45

EFFECT OF FRACTION B ON KIDNEY MALONDIALDEHYDE (MDA) IN DIABETIC RATS AFTER 8 WEEKS OF TREATMENT

| GROUP NAME | MDA (mmol/100 g tissue) | % MDA |
|---|---|---|
| NORMAL CONTROL RATS (NC) | 0.811 ± 0.083 | 100% |
| DIABETIC CONTROL RATS (DC) | 2.23 ± 0.086 [a] | 175% increase above normal |
| DIABETIC RATS (D) + FRACTION B (D + FB) | 1.07 ± 0.132 [a,b] | 32% increase above normal |

[a] significant difference from normal control
[b] significant difference from diabetic

TABLE 46

Significance Levels for Table 45

| GROUP NAME | SIGNIFICANCE LEVEL |
|---|---|
| NC Vs DC | 0.002 |
| DC Vs D + FB | 0.003 |
| NC Vs D + FB | 0.020 |

TABLE 47

EFFECT OF FRACTION B ON KIDNEY CATALASE IN DIABETIC RATS AFTER 8 WEEKS OF TREATMENT

| GROUP NAME | CATALASE (U/mg protein) | % CATALASE |
|---|---|---|
| NORMAL CONTROL RATS (NC) | 0.618 ± 0.034 | 100% |
| DIABETIC CONTROL RATS (DC) | 0.374 ± 0.030 [a] | 60% ie, 40% reduction |
| DIABETIC RATS (D) + FRACTION B (D + FB) | 0.538 ± 0.018 [a,b] | 87% ie, 13% reduction |

[a] significant difference from normal control
[b] significant difference from diabetic

TABLE 48

Significance Levels for Table 47

| GROUP NAME | SIGNIFICANCE LEVEL |
|---|---|
| NC Vs DC | 0.000 |
| DC Vs D + FB | 0.001 |
| NC Vs D + FB | 0.002 |

TABLE 49

EFFECT OF FRACTION B ON LIVER ALKALINE PHOSPHATASE (ALP) IN DIABETIC RATS AFTER 8 WEEKS OF TREATMENT

| GROUP NAME | ALP (µmoles/mg protein) | % ALP |
|---|---|---|
| NORMAL CONTROL (NC) | 0.597 ± 0.062 | 100% |
| DIABETIC CONTROL (DC) | 1.003 ± 0.028 [a] | 68% increase above normal |
| DIABETIC + FRACTION B (D + FB) | 0.636 ± 0.017 [a,b] | 6% increase above normal |

[a] significant difference from normal control
[b] significant difference from diabetic

TABLE 50

Significance Levels for Table 49

| GROUP NAME | SIGNIFICANCE LEVEL |
|---|---|
| NC Vs DC | 0.000 |
| DC Vs D + FB | 0.000 |
| NC Vs D + FB | 0.073 |

TABLE 51

EFFECT OF FRACTION B ON HEART ASPARTATE AMINOTRANSFERASE (SGOT) IN DIABETIC RATS AFTER 8 WEEKS OF TREATMENT

| GROUP NAME | SGOT (µmoles/mg protein) | % SGOT |
|---|---|---|
| NORMAL CONTROL RATS (NC) | 4.88 ± 0.434 | 100% |
| DIABETIC CONTROL RATS (DC) | 2.50 ± 0.283 [a] | 51% ie, 49% reduction |
| DIABETIC RATS (D) + FRACTION B (D + FB) | 3.24 ± 0.281 [a,b] | 66% ie, 34% reduction |

[a] significant difference from normal control
[b] significant difference from diabetic control

TABLE 52

Significance Levels for Table 51

| GROUP NAME | SIGNIFICANCE LEVEL |
|---|---|
| NC Vs DC | 0.000 |
| DC Vs D + FB | 0.000 |
| NC Vs D + FB | 0.023 |

TABLE 53

EFFECT OF FRACTION B ON HEART LACTATE DEHYDROGENASE (LDH) IN DIABETIC RATS AFTER 8 WEEKS OF TREATMENT

| GROUP NAME | LDH (μmoles/mg protein) | % LDH |
|---|---|---|
| NORMAL CONTROL RATS (NC) | 0.966 ± 0.092 | 100% |
| DIABETIC CONTROL RATS (DC) | 0.729 ± 0.048$^a$ | 75% ie, 25% reduction |
| DIABETIC RATS (D) + FRACTION B (D +FB) | 0.923 ± 0.028$^{b,c}$ | 96% ie, 4% reduction |

$^a$significant difference from normal control $^b$significant difference from diabetic control

TABLE 54

Significance Levels for Table 53

| GROUP NAME | SIGNIFICANCE LEVEL |
|---|---|
| NC Vs DC | 0.009 |
| DC Vs D + FB | 0.021 |
| NC Vs D + FB | 0.051 |

TABLE 55

EFFECT OF FRACTION B ON URINE CREATININE IN DIABETIC RATS AFTER 8 WEEKS OF TREATMENT

| GROUP NAME | CREATININE (mg/24 hr) | % CREATININE |
|---|---|---|
| NORMAL CONTROL RATS (NC) | 3.34 ± 0.271 | 100% |
| DIABETIC CONTROL RATS (DC) | 18.00 ± 2.024$^a$ | 438% increase above normal |
| DIABETIC RATS (D) + FRACTION B (D + FB) | 10.22 ± 1.221$^{a,b}$ | 206% increase above normal |

$^a$significant difference from normal control $^b$significant difference from diabetic control

TABLE 56

Significance Levels for Table 55

| GROUP NAME | SIGNIFICANCE LEVEL |
|---|---|
| NC Vs DC | 0.000 |
| DC Vs D + FB | 0.025 |
| NC Vs D + FB | 0.008 |

TABLE 57

Effect Of Fraction B On Urine Uric Acid In Diabetic Rats After 8 Weeks Of Treatment

| GROUP NAME | Urine uric acid (mg/24 hr) | % Urine uric acid |
|---|---|---|
| NORMAL CONTROL RATS (NC) | 1.29 ± 0.056 | 100% |
| DIABETIC CONTROL RATS (DC) | 4.41 ± 0.013$^a$ | 242% increase above normal |
| DIABETIC RATS (D) + FRACTION B (D + FB) | 2.28 ± 0.108$^{a,b}$ | 76% increase above normal |

$^a$significant difference from normal control $^b$significant difference from diabetic control

TABLE 58

Significance Levels for Table 57

| GROUP NAME | SIGNIFICANCE LEVEL |
|---|---|
| NC Vs DC | 0.000 |
| DC Vs D + FB | 0.002 |
| NC Vs D + FB | 0.035 |

TABLE 59

EFFECT OF FRACTION B ON WATER INTAKE IN DIABETIC RATS AFTER 8 WEEKS OF TREATMENT

| GROUP NAME | WATER INTAKE (ml/24 hr) | % WATER INTAKE |
|---|---|---|
| NORMAL CONTROL RATS (NC) | 30 ± 0.548 | 100% |
| DIABETIC CONTROL RATS (DC) | 250 ± 2.216$^a$ | 733% increase above normal |
| DIABETIC RATS (D) + FRACTION B (D + FB) | 180 ± 1.972$^{a,b}$ | 500% increase above normal |

$^a$significant difference from normal control bsignificant difference from diabetic control

TABLE 60

Significance Levels for Table 59

| GROUP NAME | SIGNIFICANCE LEVEL |
|---|---|
| NC Vs DC | 0.008 |
| DC Vs D + FB | 0.043 |
| NC Vs D + FB | 0.023 |

TABLE 61

EFFECT OF FRACTION B ON FOOD INTAKE IN DIABETIC RATS AFTER 8 WEEKS OF TREATMENT

| GROUP NAME | FOOD INTAKE (g/24 hr) | % FOOD INTAKE |
|---|---|---|
| NORMAL CONTROL RATS (NC) | 20 ± 0.328 | 100% |
| DIABETIC CONTROL RATS (DC) | 38 ± 0.216$^a$ | 90% increase above normal |
| DIABETIC RATS(D) + FRACTION B (D + FB) | 30 ± 0.387$^{a,b}$ | 50% increase above normal |

$^a$significant difference from normal control $^b$significant difference from diabetic control

TABLE 62

Significance Levels for Table 61

| GROUP NAME | SIGNIFICANCE LEVEL |
|---|---|
| NC Vs DC | 0.008 |
| DC Vs D + FB | 0.043 |
| NC Vs D + FB | 0.023 |

TABLE 63

EFFECT OF FRACTION B ON SERUM LDL
IN DIABETIC RATS AFTER 8 WEEKS OF TREATMENT

| GROUP NAME | HDL (mmol/l) | % HDL |
|---|---|---|
| NORMAL CONTROL RATS (NC) | 0.237 ± 0.007 | 100% |
| DIABETIC CONTROL RATS (DC) | 1.432 ± 0.037$^a$ | 504% increase |
| DIABETIC + FRACTION B (D + FB) | 0.917 ± 0.017$^{a,b}$ | 287% increase |

$^a$significant difference from normal control
$^b$significant difference from diabetic control
$^c$no significant difference from normal control

TABLE 64

Significance Levels for Table 63

| GROUP NAME | SIGNIFICANCE LEVEL |
|---|---|
| NC Vs DC | 0.014 |
| DC Vs D + FB | 0.023 |
| NC Vs D + FB | 0.024 |

It is to be understood that the method for treating diabetes is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method for treating diabetes, comprising:
   providing a therapeutic composition, the therapeutic composition including a soluble protein fraction prepared by fractionating epidermal gel secretions of catfish; and
   administering a therapeutically effective amount of the therapeutic composition to a patient suffering from diabetes, wherein the therapeutic composition is administered by subcutaneous injection.

2. The method according to claim 1, wherein the soluble protein fraction includes about 87% soluble proteins and about 13% lipids.

3. The method according to claim 1, wherein the fractionating comprises:
   mixing the epidermal gel secretions with an extraction buffer to provide an extract;
   homogenizing the extract with a homogenizer to provide a homogenate; and
   centrifuging the homogenate to provide the soluble protein fraction and an insoluble protein fraction.

4. The method according to claim 3, wherein the extraction buffer comprises phosphate buffered saline.

5. The method according to claim 4, wherein the fractionating further comprises:
   fractionating the insoluble protein fraction to provide an additional soluble protein fraction and an additional insoluble protein fraction; and
   adding the additional soluble protein fraction to the soluble protein fraction obtained by fractionating the epidermal gel secretions.

6. The method according to claim 4, further comprising determining whether the soluble protein fraction includes about 87% soluble proteins and about 13% lipids.

7. The method according to claim 6, further comprising adding at least one additional lipid fraction to the soluble protein fraction.

8. The method according to claim 1, wherein the catfish is Arabian Gulf catfish.

9. The method according to claim 1, wherein the therapeutically effective amount includes about 3 mg to about 3.5 mg of the soluble protein fraction per 100 gm of body weight of the patient.

10. A method for treating diabetes, comprising:
    providing a therapeutic composition, the therapeutic composition including a soluble protein fraction prepared by fractionating epidermal gel secretions of catfish, the soluble protein fraction including about 87% soluble proteins and about 13% lipids; and
    administering a therapeutically effective amount of the therapeutic composition to a patient suffering from diabetes, wherein the therapeutic composition is administered by intraperitoneal injection.

11. The method according to claim 10, wherein the fractionating comprises:
    mixing the epidermal gel secretions with an extraction buffer to provide an extract;
    homogenizing the extract with a homogenizer to provide a homogenate; and
    centrifuging the homogenate to provide the soluble protein fraction and an insoluble protein fraction.

12. The method according to claim 10, wherein the extraction buffer comprises phosphate buffered saline.

13. The method according to claim 10, wherein the catfish is Arabian Gulf catfish.

14. The method according to claim 10, wherein the therapeutically effective amount includes about 3 mg to about 3.5 mg of the soluble protein fraction per 100 gm of body weight of the patient.

15. The method according to claim 10, wherein the composition is administered while the composition is at a temperature of about 4° C.

16. A method for treating diabetes, comprising:
    providing a therapeutic composition, the therapeutic composition including a soluble protein fraction prepared by fractionating epidermal gel secretions of catfish; and
    administering a therapeutically effective amount of the therapeutic composition to a patient suffering from diabetes, wherein the therapeutic composition is administered by intraperitoneal injection.

* * * * *